(12) United States Patent
Watanabe

(10) Patent No.: US 12,705,743 B2
(45) Date of Patent: Aug. 11, 2026

(54) MEDICAL IMAGE PROCESSING DEVICE AND ENDOSCOPE SYSTEM

(71) Applicant: FUJIFILM Corporation, Tokyo (JP)

(72) Inventor: Hiroki Watanabe, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 294 days.

(21) Appl. No.: 18/518,373

(22) Filed: Nov. 22, 2023

(65) Prior Publication Data

US 2024/0087125 A1 Mar. 14, 2024

Related U.S. Application Data

(63) Continuation of application No. PCT/JP2022/018433, filed on Apr. 21, 2022.

(30) Foreign Application Priority Data

May 27, 2021 (JP) ................................ 2021-089591

(51) Int. Cl.
*G06T 7/00* (2017.01)
*A61B 1/00* (2006.01)
(Continued)

(52) U.S. Cl.
CPC ........ *G06T 7/0014* (2013.01); *A61B 1/00045* (2013.01); *A61B 1/0638* (2013.01); (Continued)

(58) Field of Classification Search
None
See application file for complete search history.

(56) References Cited

U.S. PATENT DOCUMENTS

2019/0374088 A1* 12/2019 Watanabe ............ A61B 1/0638
2020/0279368 A1* 9/2020 Tada .................. A61B 1/00016
(Continued)

FOREIGN PATENT DOCUMENTS

EP 3895597 10/2021
JP 2020065685 4/2020
(Continued)

OTHER PUBLICATIONS

"International Search Report (Form PCT/ISA/210) of PCT/JP2022/018433", mailed on Jul. 26, 2022, with English translation thereof, pp. 1-5.

(Continued)

*Primary Examiner* — Amandeep Saini
*Assistant Examiner* — Caroline Tabancay Duffy
(74) *Attorney, Agent, or Firm* — JCIPRNET

(57) ABSTRACT

The medical image processing device acquires the plurality of types of medical images obtained by imaging a subject under imaging conditions different from each other. In a case where a first medical image that is one type of the plurality of types of medical images is input, diagnosis information regarding a diagnosis of the subject shown in the first medical image is generated. Diagnostic reference information is generated using assigned reference information that is the reference information assigned to a second medical image which is included in the medical image and which has a type different from the first medical image.

14 Claims, 21 Drawing Sheets

(51) Int. Cl.
*A61B 1/06* (2006.01)
*H04N 23/74* (2023.01)

(52) U.S. Cl.
CPC ... *H04N 23/74* (2023.01); *G06T 2207/10064* (2013.01); *G06T 2207/10068* (2013.01); *G06T 2207/10152* (2013.01); *G06T 2207/30004* (2013.01)

(56) References Cited

U.S. PATENT DOCUMENTS

| | | | | |
|---|---|---|---|---|
| 2021/0259515 | A1* | 8/2021 | Makino | A61B 1/00004 |
| 2021/0407077 | A1* | 12/2021 | Makino | G16H 30/40 |
| 2022/0020147 | A1 | 1/2022 | Sasada et al. | |
| 2022/0237795 | A1 | 7/2022 | Watanabe | |

FOREIGN PATENT DOCUMENTS

| | | | | |
|---|---|---|---|---|
| WO | WO-2020036109 | A1 * | 2/2020 | G02B 23/24 |
| WO | 2020116115 | | 6/2020 | |
| WO | 2020121906 | | 6/2020 | |
| WO | 2021079691 | | 4/2021 | |

OTHER PUBLICATIONS

"Written Opinion of the International Searching Authority (Form PCT/ISA/237) of PCT/ JP2022/018433", mailed on Jul. 26, 2022, with English translation thereof, pp. 1-12.

"Office Action of Japan Counterpart Application", issued on Sep. 24, 2025, with English translation thereof, pp. 1-14.

* cited by examiner

FIG. 2

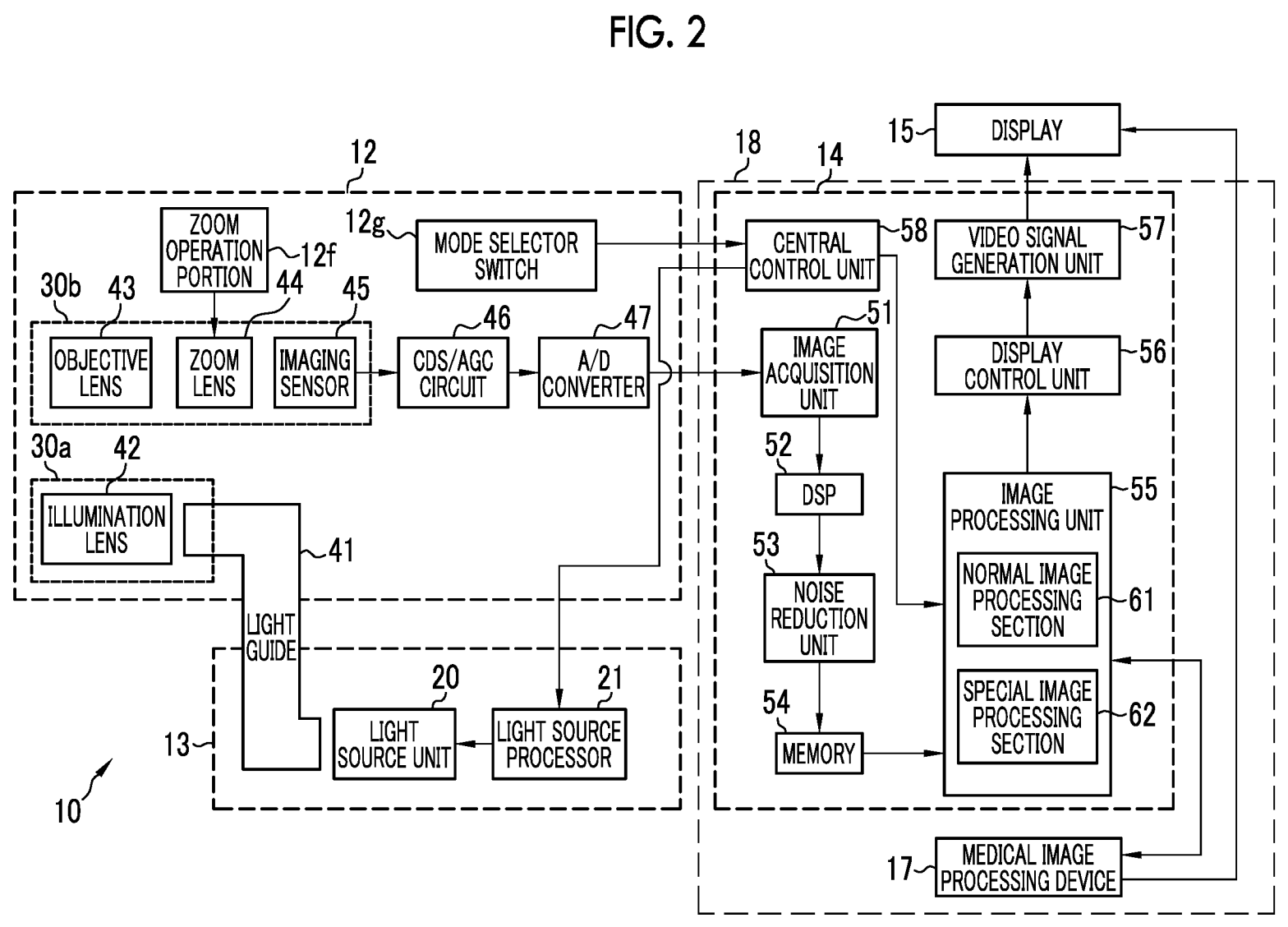

10
12
12f
12g
13
14
15
17
18
30a
30b
DISPLAY
VIDEO SIGNAL GENERATION UNIT 57
DISPLAY CONTROL UNIT 56
IMAGE PROCESSING UNIT 55
NORMAL IMAGE PROCESSING SECTION 61
SPECIAL IMAGE PROCESSING SECTION 62
MEDICAL IMAGE PROCESSING DEVICE
CENTRAL CONTROL UNIT 58
IMAGE ACQUISITION UNIT 51
DSP 52
NOISE REDUCTION UNIT 53
MEMORY 54
MODE SELECTOR SWITCH
A/D CONVERTER 47
CDS/AGC CIRCUIT 46
IMAGING SENSOR 45
ZOOM LENS 44
OBJECTIVE LENS 43
ZOOM OPERATION PORTION
ILLUMINATION LENS 42
LIGHT GUIDE 41
LIGHT SOURCE PROCESSOR 21
LIGHT SOURCE UNIT 20

17
MEDICAL IMAGE ACQUISITION UNIT
81
DIAGNOSIS INFORMATION GENERATION UNIT
82
FIRST DIAGNOSIS MODEL
91
REFERENCE INFORMATION GENERATION UNIT
83
REFERENCE CONVERTER
92
FINDING INFORMATION STORAGE SECTION
93
INFORMATION OUTPUT UNIT
84
DISPLAY CONTROL UNIT
85
PROCESSOR DEVICE
14
DISPLAY
15

94

| FINDING INFORMATION | | | | | |
|---|---|---|---|---|---|
| IMAGE NUMBER | ERYTHEMA | VISIBLE VASCULAR PATTERN | ULCERATION | ENDOSCOPIC SEVERITY | |
| W000001 | 1 | 0 | 0 | Mayo 1 | |
| W000002 | 0 | 0 | 0 | Mayo 0 | |
| W000003 | 3 | 3 | 1 | Mayo 3 | |
| W000004 | 2 | 0 | 1 | Mayo 2 | |
| | | | | | |

17
81
MEDICAL IMAGE ACQUISITION UNIT
82
DIAGNOSIS INFORMATION GENERATION UNIT
FIRST DIAGNOSIS MODEL
91
83
REFERENCE INFORMATION GENERATION UNIT
FIRST REFERENCE CONVERTER
92X
FINDING INFORMATION STORAGE SECTION
93
FIRST FEATURE AMOUNT MODEL
95
84
INFORMATION OUTPUT UNIT
85
DISPLAY CONTROL UNIT
14
PROCESSOR DEVICE
15
DISPLAY

| FINDING INFORMATION | | | | | FEATURE AMOUNT | | | |
|---|---|---|---|---|---|---|---|---|
| IMAGE NUMBER | ERYTHEMA | VISIBLE VASCULAR PATTERN | ULCERATION | ENDOSCOPIC SEVERITY | IMAGE NUMBER | A | B | C |
| W000001 | 1 | 0 | 0 | Mayo 1 | B000001 | 11 | 5 | 0 |
| W000002 | 0 | 0 | 0 | Mayo 0 | B000002 | 2 | 2 | 0 |
| W000003 | 3 | 3 | 1 | Mayo 3 | B000003 | 98 | 88 | 12 |
| W000004 | 2 | 0 | 1 | Mayo 2 | B000004 | 60 | 49 | 2 |

Figure 13:
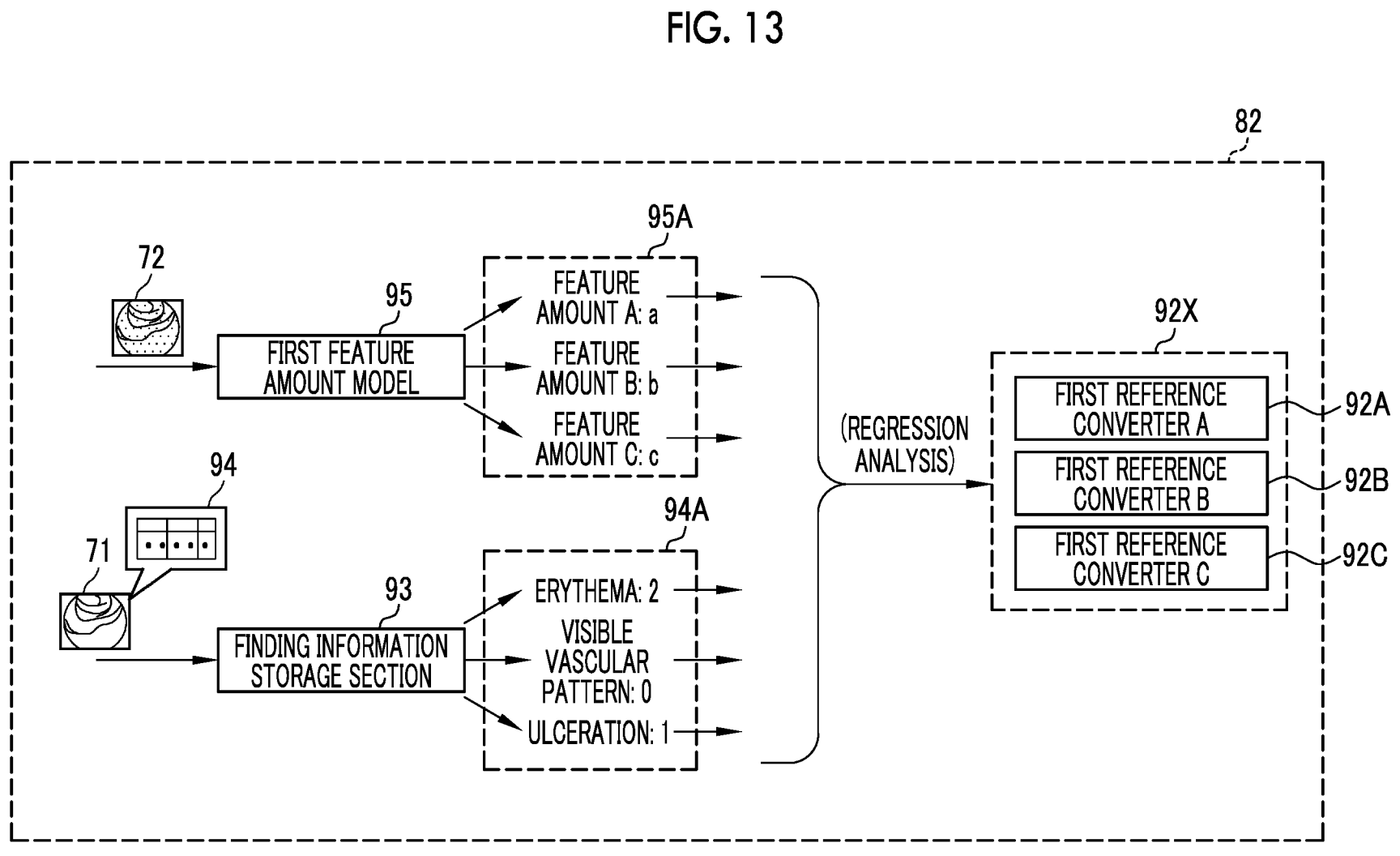

92A FIRST REFERENCE CONVERTER A

92B FIRST REFERENCE CONVERTER B

92C FIRST REFERENCE CONVERTER C (REGRESSION ANALYSIS)

95A

FEATURE AMOUNT A: a

FEATURE AMOUNT B: b

FEATURE AMOUNT C: c

94A

ERYTHEMA: 2

VISIBLE VASCULAR PATTERN: 0

ULCERATION: 1

95 FIRST FEATURE AMOUNT MODEL

93 FINDING INFORMATION STORAGE SECTION

72

94

71

82
72
91
FIRST DIAGNOSIS MODEL
91A
Mayo 2
84
INFORMATION OUTPUT UNIT
83
72
95
FIRST FEATURE AMOUNT MODEL
95A
FEATURE AMOUNT D
FEATURE AMOUNT E
FEATURE AMOUNT F
92A
FIRST REFERENCE CONVERTER A
FIRST REFERENCE CONVERTER B
92B
FIRST REFERENCE CONVERTER C
92C
92Y
ERYTHEMA: 50
VISIBLE VASCULAR PATTERN: 0
ULCERATION: 30

17
81
MEDICAL IMAGE ACQUISITION UNIT
82
DIAGNOSIS INFORMATION GENERATION UNIT
FIRST DIAGNOSIS MODEL
91
83
REFERENCE INFORMATION GENERATION UNIT
FIRST REFERENCE CONVERTER
92X
FINDING INFORMATION STORAGE SECTION
93
FIRST FEATURE AMOUNT ACQUISITION SECTION
100
84
INFORMATION OUTPUT UNIT
85
DISPLAY CONTROL UNIT
14
PROCESSOR DEVICE
15
DISPLAY 82
72
91
FIRST DIAGNOSIS MODEL
91A
Mayo 2
84
INFORMATION OUTPUT UNIT
83
95A
FEATURE AMOUNT G
FEATURE AMOUNT H
FEATURE AMOUNT I
92A
FIRST REFERENCE CONVERTER A
FIRST REFERENCE CONVERTER B
92B
FIRST REFERENCE CONVERTER C
92C
92Y
ERYTHEMA: 50
VISIBLE VASCULAR PATTERN: 0
ULCERATION: 30

17
MEDICAL IMAGE ACQUISITION UNIT
81
DIAGNOSIS INFORMATION GENERATION UNIT
82
FIRST DIAGNOSIS MODEL
91
INFORMATION OUTPUT UNIT
84
DISPLAY CONTROL UNIT
85
REFERENCE INFORMATION GENERATION UNIT
83
SECOND REFERENCE CONVERTER
120
FINDING INFORMATION STORAGE SECTION
93
SECOND FEATURE AMOUNT MODEL
110
PROCESSOR DEVICE
14
DISPLAY
15

82
72
91
FIRST DIAGNOSIS MODEL
91A
Mayo 2
84
INFORMATION OUTPUT UNIT
83
71
110
SECOND FEATURE AMOUNT MODEL
110A
FEATURE AMOUNT J
FEATURE AMOUNT K
FEATURE AMOUNT L
120A
SECOND REFERENCE CONVERTER A
120B
SECOND REFERENCE CONVERTER B
120C
SECOND REFERENCE CONVERTER C
92Y
ERYTHEMA: 50
VISIBLE VASCULAR PATTERN: 0
ULCERATION: 30

MEDICAL IMAGE PROCESSING DEVICE AND ENDOSCOPE SYSTEM

CROSS-REFERENCE TO RELATED APPLICATIONS

This application is a Continuation of PCT International Application No. PCT/JP2022/018433 filed on 21 Apr. 2022, which claims priority under 35 U.S.C. § 119(a) to Japanese Patent Application No. 2021-089591 filed on 27 May 2021. The above application is hereby expressly incorporated by reference, in its entirety, into the present application.

BACKGROUND OF THE INVENTION

1. Field of the Invention

The present invention relates to a medical image processing device and an endoscope system that provide diagnosis information and reference information.

2. Description of the Related Art

A computer-aided diagnosis (CAD) technique for determining stages and other factors of diseases by performing appropriate image processing on an endoscopic image has been developed. In the CAD based on image processing, instead of a doctor, a processor of a computer calculates a visual appearance (endoscopic features) by using an image (hereinafter, referred to as an endoscopic image) obtained by imaging an observation target, which is a subject, with an endoscope, and via diagnostic methods, it discerns the content (pathology) of the observation target. As described above, in the CAD based on image processing, the severity of diseases is estimated on the basis of a quantified feature amount of the feature of the visual appearance, such as the shape of blood vessels, which is comprehensible to a human being such as a doctor. Therefore, the doctor can comprehend the estimation rationale of the CAD.

On the other hand, in the CAD based on image processing, there are cases where, in a case where there are variations in the endoscopic image, such as the distance or angle between a scope and a target, the presence or absence of halation, or the presence or absence of water bubbles, the numerical value of the feature amount to be calculated changes, which may make it difficult to obtain an accurate estimation result in the CAD and make it difficult to expect high accuracy for images other than images captured under defined conditions.

Recently, a CAD technique based on artificial intelligence (AI) using machine learning or the like has been developed. In the CAD based on AI, irrespective of diagnostic methods, AI itself finds out the feature of the visual appearance with a high correlation between the visual appearance and the content, and calculates and outputs the content as the estimation result corresponding to the finding. In this way, since diagnostic methods are ignored in the CAD based on AI, the human being cannot interpret what kind of features the CAD has used as a basis to make a determination for reaching the estimation result.

In response to this, for example, there is known an information processing apparatus comprising a model that outputs a determination result related to a diagnosis of a disease as well as a region contributing to the determination or a diagnosis reference prediction in a case where an endoscopic image is input (WO2020/116115A1).

SUMMARY OF THE INVENTION

In the CAD based on AI, there exists a so-called black box problem, that is, the human being cannot interpret what kind of features the CAD has used as a basis to make a determination. On the other hand, there also exists an advantage in that having learned such various scenes can ensure sufficient accuracy of the estimation result even in a case where there are variations in the endoscopic image such as the distance or angle between the scope and the observation target, the presence or absence of halation, or the presence or absence of water bubbles.

In order to further enhance the accuracy of the estimation result in the CAD based on AI, it is necessary to perform calculation by using feature amounts that cannot be grasped or managed by the human being to more complexly combine the feature amounts, but it is considered that this makes it more difficult to explain what kind of features the human being has used as a basis to make a determination. That is, it can be said that there is a trade-off relationship between the "explainability of determination" and "high accuracy" in the CAD based on AI.

Therefore, there is a demand for the development of CAD that achieves both the "explainability of determination", which is the advantage of the CAD based on image processing, and "high accuracy", which is the advantage of the CAD based on AI.

An object of the present invention is to provide a medical image processing device and an endoscope system that can obtain diagnosis information and reference information regarding a reference for a diagnosis with excellent accuracy by using a plurality of types of medical images.

According to an aspect of the present invention, there is provided a medical image processing device comprising a processor. The processor is configured to: acquire a plurality of types of medical images obtained by imaging a subject under imaging conditions different from each other; generate, in a case where a first medical image that is one type of the plurality of types of medical images is input, diagnosis information regarding a diagnosis of the subject shown in the first medical image; generate, in a case where the medical image showing the same subject as the subject shown in the first medical image is input, reference information regarding a reference for the diagnosis; and output the diagnosis information and the reference information in association with each other, and the reference information is generated using assigned reference information that is the reference information assigned to a second medical image which is included in the medical image and which has a type different from the first medical image.

It is preferable that the processor is configured to generate the reference information using the assigned reference information and the medical image showing the same subject as the subject shown in the second medical image to which the assigned reference information is assigned.

It is preferable that the processor is configured to, in a case where the medical image showing the same subject as the subject shown in the first medical image is input: acquire a feature amount of the input medical image; and generate the reference information by converting the feature amount into the reference information.

It is preferable that the processor is configured to, in a case where the medical image showing the same subject as the subject shown in the first medical image is input: acquire a plurality of feature amounts of the input medical image; and generate the reference information by converting the plurality of feature amounts into at least one piece of the reference information.

It is preferable that the processor includes a first model that generates the diagnosis information, and that the first model has a layered structure including a first output layer that outputs the diagnosis information and at least one first intermediate layer.

It is preferable that the processor includes a second model that generates the feature amount, and the second model has a layered structure including a second output layer that outputs the feature amount and at least one second intermediate layer, and the second intermediate layer shares the first intermediate layer.

It is preferable that the assigned reference information is the reference information assigned to the second medical image by a doctor through visual observation of the second medical image.

It is preferable that the processor is configured to, in a case where the first medical image is input, acquire a first feature amount of the first medical image and generate the diagnosis information based on the first feature amount.

It is preferable that the processor is configured to generate the reference information by converting the first feature amount into the reference information using the assigned reference information and the first medical image showing the same subject as the subject shown in the second medical image to which the assigned reference information is assigned.

It is preferable that the processor is configured to, in a case where the second medical image showing the same subject as the subject shown in the first medical image is input: acquire a second feature amount of the second medical image; and generate the reference information by converting the second feature amount into the reference information using the assigned reference information and the second medical image.

It is preferable that the processor is configured to acquire the second feature amount of the second medical image captured within a preset period before and/or after a time when the first medical image is captured.

It is preferable that the processor is configured to perform a control of displaying the first medical image and/or the second medical image on a display.

It is preferable that the processor is configured to perform a control of displaying the diagnosis information and the reference information, which are associated with each other, on the display.

It is preferable that the imaging condition is a spectrum of illumination light.

Further, according to another aspect of the present invention, there is provided an endoscope system comprising: a plurality of light sources that emit rays of light having different wavelength ranges; a processor device that includes a light source processor which performs a control of emitting each of a plurality of types of illumination light having different combinations of light intensity ratios between the plurality of light sources; an endoscope that images the subject illuminated with the illumination light; and the medical image processing device.

According to the present invention, it is possible to obtain diagnosis information and reference information regarding a reference for a diagnosis with excellent accuracy by using a plurality of types of medical images.

BRIEF DESCRIPTION OF THE DRAWINGS

FIG. 2 is a block diagram showing a function of the endoscope system.

FIG. 12 is an explanatory diagram illustrating converter information.

FIG. 13 is an explanatory diagram illustrating a generation method of a first reference converter.

DESCRIPTION OF THE PREFERRED EMBODIMENTS

Figure 1:
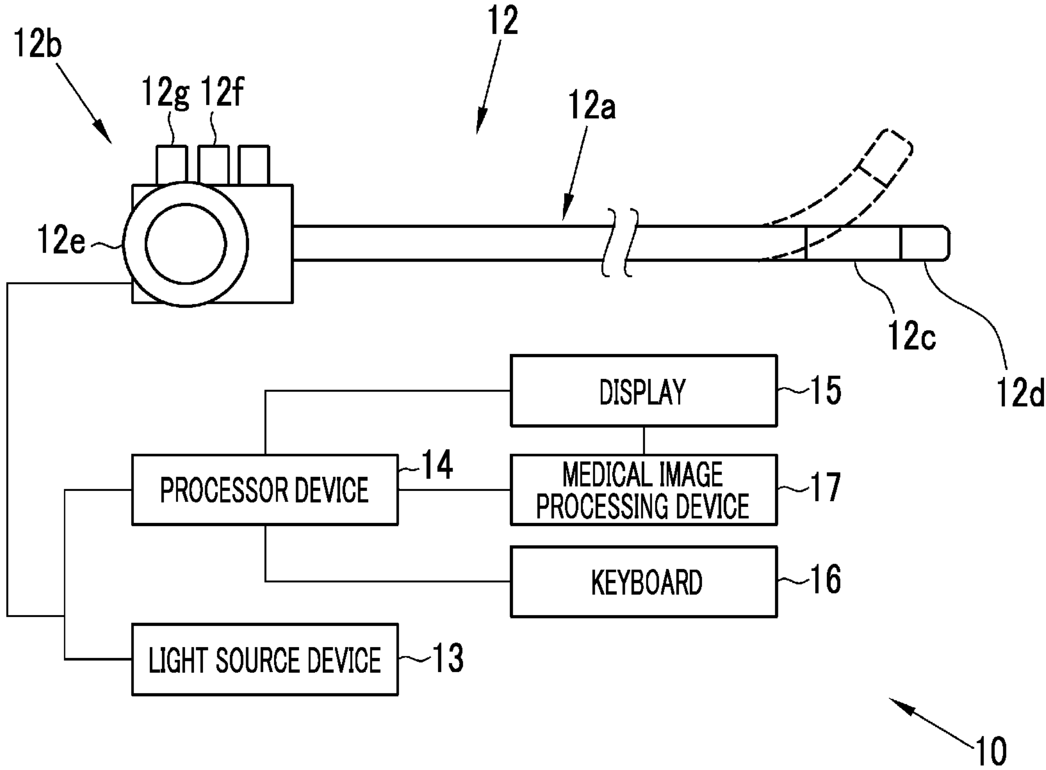
FIG. 1 is an external view of an endoscope system.

As shown in FIG. 1, an endoscope system 10 includes an endoscope 12, a light source device 13, a processor device 14, a display 15, a keyboard 16, and a medical image processing device 17. The endoscope 12 is optically connected to the light source device 13 and is electrically connected to the processor device 14. The processor device 14 is connected to the medical image processing device 17. The medical image processing device 17 acquires an endoscopic image that is a medical image from the processor device 14, and performs various types of processing for acquiring various types of information and the like.

In the present embodiment, the medical image is the endoscopic image. In addition, in the present embodiment, the medical image processing device 17 and the processor device 14 are separate devices, but the processor device 14 may perform functions of the medical image processing device 17 by disposing a device that performs the functions of the medical image processing device 17 inside the processor device 14. Further, various connections are not limited to wired connections, and may be wireless connections, or may be connections via a network. Therefore, the functions of the medical image processing device 17 may be performed by an external device connected via the network.

The endoscope 12 includes an insertion part 12*a* to be inserted into a body of a subject under examination having an observation target, an operation part 12*b* provided at a proximal end portion of the insertion part 12*a*, and a bending portion 12*c* and a distal end portion 12*d* provided on a distal end side of the insertion part 12*a*. By operating an angle knob 12*e* (see FIG. 2) of the operation part 12*b*, the bending portion 12*c* performs a bending movement. The distal end portion 12*d* is directed in a desired direction by the bending movement of the bending portion 12*c*.

The operation part 12*b* includes, in addition to the angle knob 12*e*, a zoom operation portion 12*f* for changing an imaging magnification and a mode selector switch 12*g* used for a switching operation of an observation mode. The switching operation of the observation mode or the zoom operation may be an operation or an instruction using the keyboard 16, a footswitch (not shown), or the like in addition to the mode selector switch 12*g* or the zoom operation portion 12*f*.

The endoscope system 10 has three observation modes: a normal observation mode; a special observation mode; and a diagnosis support observation mode. The normal observation mode is a mode in which a normal image, which is a natural color-tone image obtained by imaging the observation target using white light as illumination light, is displayed on the display 15. The special observation mode includes a first special observation mode. The first special observation mode is a mode in which a first medical image (hereinafter, referred to as a first image) in which surface layer information, such as surface layer blood vessels, is enhanced is displayed on the display 15.

The diagnosis support observation mode is a mode in which the normal image and/or the first image, and diagnosis information regarding a diagnosis of the observation target and reference information regarding a reference for the diagnosis, which are generated and output by the medical image processing device 17, are displayed on the display 15. The diagnosis information is information that is generated and output by the medical image processing device 17 regarding the diagnosis of the observation target based on the endoscopic image. In addition, the reference information is information that is generated and output by the medical image processing device 17 regarding the reference for the diagnosis of the observation target based on the endoscopic image. The diagnosis information and the reference information are information regarding the diagnosis of the observation target, which is a subject shown in the endoscopic image, and the reference related to the diagnosis and are information for supporting a diagnosis of a doctor. In a case where the doctor performs a diagnosis while viewing the normal image and/or the first image displayed on the display 15 through display of the diagnosis information and the reference information on the display 15 or the like, the displayed diagnosis information and reference information are used to support the doctor's diagnosis.

The processor device 14 is electrically connected to the display 15 and the keyboard 16. The display 15 displays, for example, the normal image, the first image, the diagnosis information, and the reference information, and/or information attached to these. The keyboard 16 functions as a user interface that accepts an input operation, such as function settings. An external storage (not shown) that stores images, image information, or the like may be connected to the processor device 14.

As shown in FIG. 2, the light source device 13 emits illumination light to be emitted to the observation target and comprises a light source unit 20 and a light source processor 21 that controls the light source unit 20. The light source unit 20 is composed of, for example, a semiconductor light source such as multi-color light emitting diodes (LEDs), a combination of a laser diode and a phosphor, or a xenon lamp or a halogen light source. Additionally, the light source unit 20 includes, for example, an optical filter for adjusting the wavelength range of light emitted by the LED or the like. The light source processor 21 controls the amount of illumination light by turning on/off each LED or the like or adjusting a drive current and a drive voltage of each LED or the like. Further, the light source processor 21 controls the wavelength range of illumination light by changing the optical filter or the like.

Figure 3:
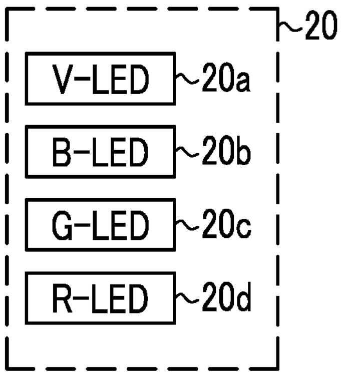
FIG. 3 is an explanatory diagram illustrating four-color LEDs provided in a light source unit.

As shown in FIG. 3, in the present embodiment, the light source unit 20 has four-color LEDs, that is, a violet light emitting diode (V-LED) 20*a*, a blue light emitting diode (B-LED) 20*b*, a green light emitting diode (G-LED) 20*c*, and a red light emitting diode (R-LED) 20*d*.

Figure 4:
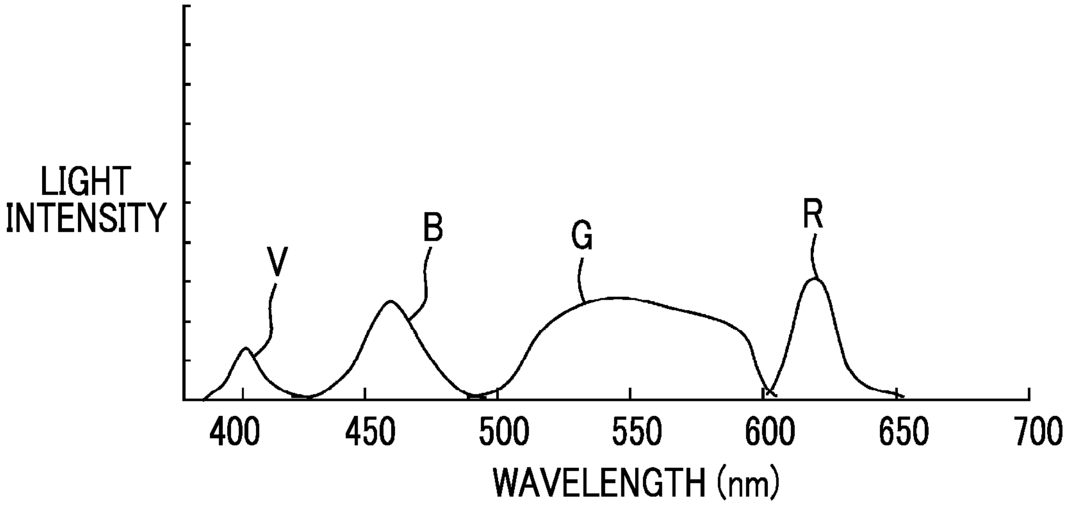
FIG. 4 is a graph showing spectra of violet light V, blue light B, green light G, and red light R.

As shown in FIG. 4, the V-LED 20*a* generates violet light V with a central wavelength of 410±10 nm and a wavelength range of 380 to 420 nm. The B-LED 20*b* generates blue light B with a central wavelength of 450±10 nm and a wavelength range of 420 to 500 nm. The G-LED 20*c* generates green light G with a wavelength range of 480 to 600 nm. The R-LED 20*d* generates red light R with a central wavelength of 620 to 630 nm and a wavelength range of 600 to 650 nm.

The light source processor 21 controls the V-LED 20*a*, the B-LED 20*b*, the G-LED 20*c*, and the R-LED 20*d*. The light source processor 21 controls the respective LEDs 20*a* to 20*d* to emit normal light of which the combination of light intensity ratios between the violet light V, the blue light B, the green light G, and the red light R is Vc:Bc:Gc:Rc during the normal observation mode.

Figure 5:
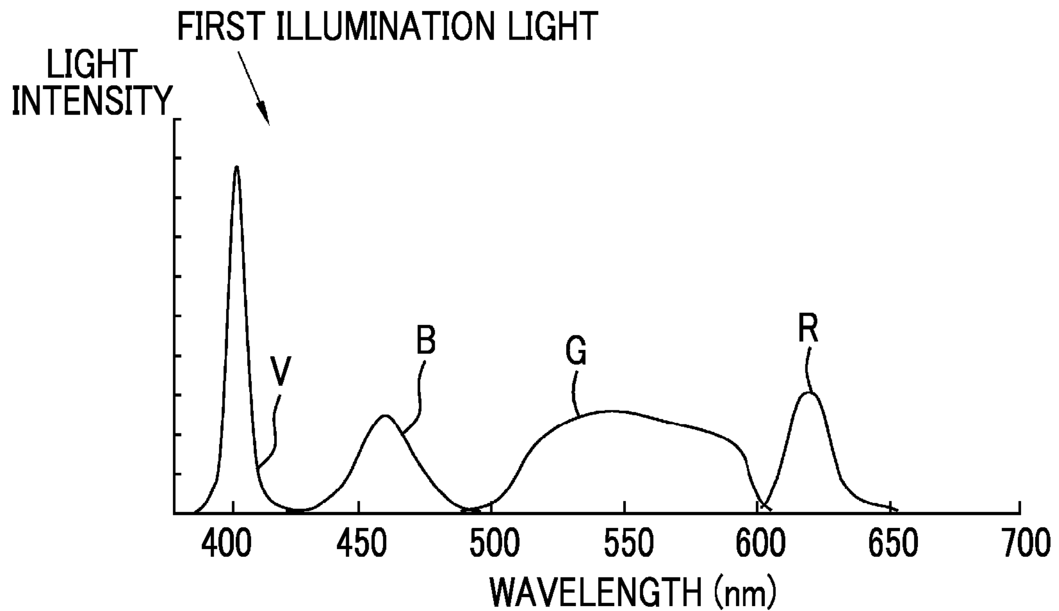
FIG. 5 is a graph showing a spectrum of first illumination light.

The light source processor 21 controls the respective LEDs 20*a* to 20*d* to emit first illumination light of which the combination of the light intensity ratios between the violet light V, the blue light B, the green light G, and the red light R is Vs1:Bs1:Gs1:Rs1 is emitted in a case where the first special observation mode is set. It is preferable that the first illumination light enhances surface layer blood vessels. Therefore, it is preferable for the light intensity of the violet light V of the first illumination light to be greater than the light intensity of the blue light B. For example, as shown in FIG. 5, a ratio between a light intensity Vs1 of the violet light V and a light intensity Bs1 of the blue light B is set to "4:1".

In the present specification, the combinations of the light intensity ratios include a case where the ratio of at least one semiconductor light source is zero (0). Therefore, a case where any one or two or more of the semiconductor light sources are not turned on is included. For example, a case where only one semiconductor light source is turned on and the other three semiconductor light sources are not turned on as in a case where the combination of the light intensity ratios between the violet light V, the blue light B, the green light G, and the red light R is 1:0:0:0 is also regarded as having light intensity ratios and is one of the combinations of the light intensity ratios.

As described above, the combinations of the light intensity ratios between the violet light V, the blue light B, the green light G, and the red light R, which are emitted in the normal observation mode or the first special observation mode, that is, the types of illumination light, are different from each other. In the diagnosis support observation mode, a plurality of different types of Illumination light are automatically switched and emitted. An observation mode using a different type of illumination light of which the combination of the light intensity ratios is different from the combinations of the light intensity ratios between rays of the illumination light used in these observation modes may be used.

The light source processor 21 switches and emits a specific type of illumination light in a case where the diagnosis support observation mode is set. Specifically, a normal light period in which the normal light is continuously emitted and a first illumination light period in which the first illumination light is continuously emitted are alternately repeated. With regard to the periods, the normal light period in which the normal light is emitted is performed for a predetermined number of frames, and then the first illumination light period in which the first illumination light is emitted is performed for a predetermined number of frames. After that, the normal light period starts again, and a set of the normal light period and the first illumination light period is repeated.

The “frame” refers to a unit for controlling an imaging sensor 45 (see FIG. 2) that images the observation target, and, for example, “one frame” refers to a period including at least an exposure period for exposing the imaging sensor 45 to light from the observation target and a readout period for reading out image signals. In the present embodiment, various periods, such as the normal light period or the first illumination light period, are each defined so as to correspond to the “frame” which is the unit of imaging.

Figure 6:
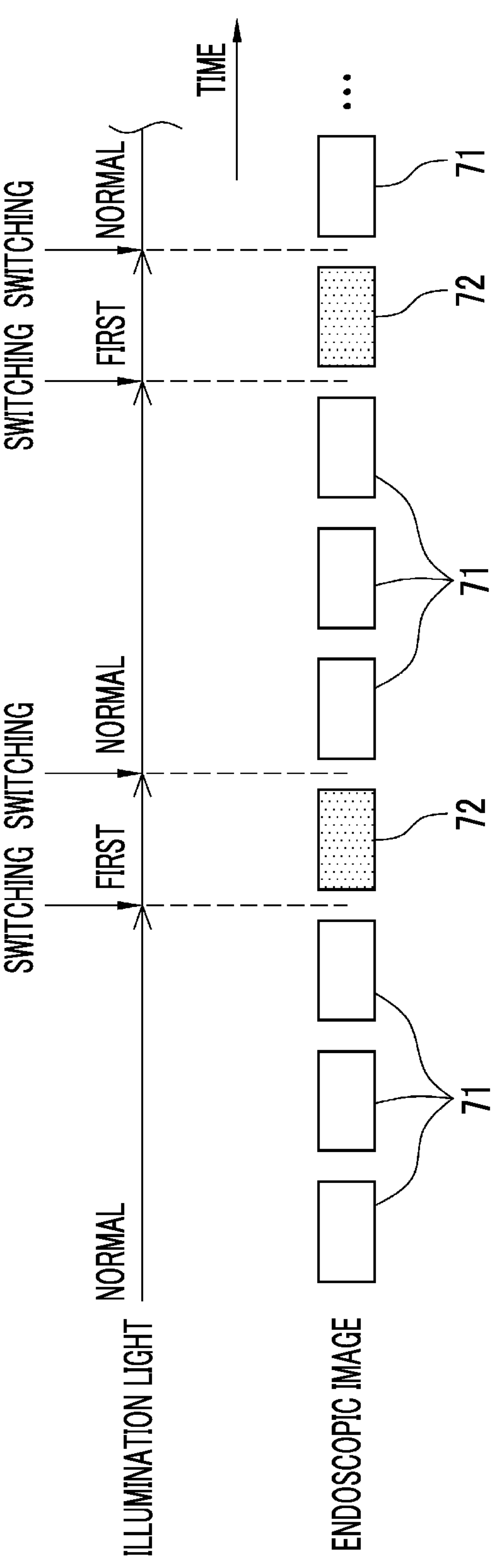
FIG. 6 is an explanatory diagram illustrating a type and an order of an endoscopic image captured by the endoscope system.

As shown in FIG. 6, in the diagnosis support observation mode, the normal light period in which the normal light indicated by “normal” in a field of illumination light is emitted is performed for a period of three frames, and then the illumination light is switched, and the first illumination light period in which the first illumination light indicated by “first” in the field of illumination light is emitted is performed for a period of one frame. After that, the normal light period starts again, and a set of the normal light period and the first illumination light period is repeated for four frames. Therefore, normal images 71 are consecutively captured three times during the normal light period of three frames, and then a first image 72 is captured once during the first illumination light period. After that, it returns to the normal light period, and this pattern is continuously repeated. In the figure, the first image 72 is indicated by being shaded because a color tone is different from that of the normal image 71.

The light emitted from each of the LEDs 20*a* to 20*d* is incident on a light guide 41 via an optical path coupling portion (not shown) composed of a mirror, a lens, or the like. The light guide 41 is incorporated into the endoscope 12 and a universal cord (a cord connecting the endoscope 12 to the light source device 13 and the processor device 14). The light guide 41 propagates light from the optical path coupling portion to the distal end portion 12*d* of the endoscope 12.

An illumination optical system 30*a* and an imaging optical system 30*b* are provided in the distal end portion 12*d* of the endoscope 12. The illumination optical system 30*a* includes an illumination lens 42, and the illumination light propagated by the light guide 41 is emitted to the observation target via the illumination lens 42. The imaging optical system 30*b* includes an objective lens 43, a zoom lens 44, and the imaging sensor 45. Various types of light such as reflected light, scattered light, and fluorescence from the observation target are incident on the imaging sensor 45 via the objective lens 43 and the zoom lens 44. As a result, an image of the observation target is formed on the imaging sensor 45. The zoom lens 44 is freely moved between a telephoto end and a wide end by operating the zoom operation portion 12*f*, thereby magnifying and reducing the observation target of which the image is formed on the imaging sensor 45.

The imaging sensor 45 is a color imaging sensor provided with any of a red (R) color filter, a green (G) color filter, or a blue (B) color filter for each pixel, and images the observation target and outputs image signals for respective RGB colors. A charge coupled device (CCD) imaging sensor or a complementary metal-oxide semiconductor (CMOS) imaging sensor can be utilized as the imaging sensor 45. Alternatively, instead of the imaging sensor 45 provided with primary color filters, a complementary color imaging sensor provided with complementary color filters, that is, cyan (C), magenta (M), yellow (Y), and green (G), may also be used. In a case where the complementary color imaging sensor is used, four-color image signals, that is, CMYG, are output. Therefore, through complementary-primary color conversion, by converting the four-color image signals, that is, CMYG, into three-color image signals, that is, RGB, it is possible to obtain RGB image signals similar to those of the imaging sensor 45. Alternatively, instead of the imaging sensor 45, a monochrome imaging sensor that is not provided with the color filters may be used.

The imaging sensor 45 is driven and controlled by an imaging control unit (not shown). The central control unit 58 (see FIG. 2) controls the light emission of the light source unit 20 through the light source processor 21 in synchronization with the imaging control unit to perform a control such that the observation target illuminated with the normal light is imaged in the normal observation mode. As a result, a Bc image signal is output from a B pixel of the imaging sensor 45, a Gc image signal is output from a G pixel, and an Rc image signal is output from an R pixel. In the first special observation mode, the central control unit 58 controls the light emission of the light source unit 20 to control the imaging sensor 45 to image the observation target illuminated with the first illumination light. As a result, in the first special observation mode, a Bs1 image signal is output from the B pixel of the imaging sensor 45, a Gs1 image signal is output from the G pixel, and an Rs1 image signal is output from the R pixel.

In addition, the diagnosis support observation mode, the central control unit 58 (see FIG. 2) controls the light emission of the light source unit 20 to control the imaging sensor 45 to image the observation target illuminated with the normal light and the first illumination light in respective preset periods. As a result, in the diagnosis support observation mode, a Bc image signal is output from the B pixel of the imaging sensor 45, a Gc image signal is output from the G pixel, and an Rc image signal is output from the R pixel, in the normal light period. In the first illumination light period, a Bs1 image signal is output from the B pixel of the imaging sensor 45, a Gs1 image signal is output from the G pixel, and an Rs1 image signal is output from the R pixel.

A correlated double sampling/automatic gain control (CDS/AGC) circuit 46 performs correlated double sampling (CDS) or automatic gain control (AGC) on an analog image signal obtained from the imaging sensor 45. The image signal that has passed through the CDS/AGC circuit 46 is converted into a digital image signal by an analog/digital (A/D) converter 47. The digital image signal after the A/D conversion is input to the processor device 14.

In the processor device 14, a program related to processing such as image processing is stored in a program memory (not shown). In the processor device 14, the program within the program memory is operated by the central control unit 58 composed of an image processor, which is a first processor, or the like, whereby the functions of an image acquisition unit 51, a digital signal processor (DSP) 52, a noise reduction unit 53, a memory 54, an image processing unit 55, a display control unit 56, a video signal generation unit 57, and the central control unit 58 are realized. Additionally, the central control unit 58 receives information from the endoscope 12 and the light source device 13, and controls each unit of the processor device 14 and controls the endoscope 12 or the light source device 13, based on the received information. Further, information, such as an instruction through the keyboard 16, is also received.

The image acquisition unit 51 acquires the digital image signal of the endoscopic image, which is input from the endoscope 12. The image acquisition unit 51 acquires, for each frame, the image signal obtained by imaging the observation target illuminated with each illumination light. The type of illumination light, that is, the spectrum of illumination light, is one of imaging conditions. In the present embodiment, as the imaging condition, the spectrum of illumination light is used, and the image acquisition unit 51 acquires a plurality of types of endoscopic images with different imaging conditions, such as the spectrum of illumination light.

Examples of the imaging conditions include the imaging time, the observation distance with the observation target, and the zoom magnification of the endoscope 12, in addition to the spectrum of illumination light, that is, the light amount ratios between LED **20*a* to 20*d*. The light amount ratios are acquired from the central control unit 58. The imaging time may be acquired from header information or the like included in the endoscopic image and may be acquired from the central control unit 58. The observation distance includes, for example, a long-distance non-magnified observation distance and a close-distance magnified observation distance and is acquired by the exposure amount, the measurement laser light, or the like obtained from the endoscopic image. The observation distance may be acquired through frequency analysis of the image. The zoom magnification of the endoscope 12 includes, for example, non-magnification for non-magnified observation, and magnification ranging from low magnification to high magnification that enables magnified observation, and can be acquired based on change operations of the zoom operation portion 12*f***.

The acquired image signal is transmitted to the DSP 52. The DSP 52 performs digital signal processing, such as color correction processing, on the received image signal. The noise reduction unit 53 performs noise reduction processing through, for example, a moving average method or a median filtering method, on the image signal on which the color correction processing or the like has been performed by the DSP 52. The noise-reduced image signal is stored in the memory 54.

The image processing unit 55 acquires the noise-reduced image signal from the memory 54. Then, signal processing, such as color conversion processing, color enhancement processing, and structure enhancement processing, is performed as necessary on the acquired image signal, and a color endoscopic image showing the observation target is generated. The image processing unit 55 comprises a normal image processing section 61 and a special image processing section 62.

In the image processing unit 55, the normal image processing section 61 performs image processing for the normal observation mode, such as the color conversion processing, the color enhancement processing, and the structure enhancement processing, on the input noise-reduced image signal for the normal image for one frame, in the normal observation mode or the diagnosis support observation mode. The image signal that has been subjected to the image processing for the normal observation mode is input to the medical image processing device 17 and/or the display control unit 56 as the normal image 71.

In the special observation mode or the diagnosis support observation mode, the special image processing section 62 performs the image processing for the first special observation mode, such as the color conversion processing, the color enhancement processing, and the structure enhancement processing, on the input noise-reduced image signal for the first image for one frame in the first special observation mode. The image signal that has been subjected to the image processing for the first special observation mode is input to the medical image processing device 17 and/or the display control unit 56 as the first image 72. The image processing unit 55 may adjust a frame rate in a case where the endoscopic image is input to the medical image processing device 17 and/or the display control unit 56.

Since the endoscopic image generated by the image processing unit 55 is the normal image 71 in a case where the observation mode is the normal observation mode, and is the first image 72 in a case where the observation mode is the first special observation mode, and the contents of the color conversion processing, the color enhancement processing, and the structure enhancement processing differ depending on the observation modes. In a case of the normal observation mode, the image processing unit 55 generates the normal image 71 by performing the above various types of signal processing to make the observation target have a natural color tone. In a case of the special observation mode, for example, the image processing unit 55 generates the first image 72 by performing the above various types of signal processing to enhance the blood vessels as the observation target.

The semiconductor light sources include the V-LED **20*a* that emits the violet light V (first narrow band light) with a central wavelength range of 410±10 nm and a wavelength range of 380 to 420 nm, and the B-LED 20*b* that emits the blue light B (second narrow band light) with a central wavelength range of 450±10 nm and a wavelength range of 420 to 500 nm. Therefore, in the first image 72 generated by the image processing unit 55, blood vessels (so-called surface layer blood vessels) or blood located at a relatively shallow position in the observation target with a surface of the mucous membrane as a reference has a magenta-based color (for example, a brown color). Therefore, in the first image 72**, the blood vessels or the bleeding (blood) of the observation target is enhanced by a difference in color against the mucous membrane represented by a pink-based color.

The display control unit 56 receives the endoscopic image generated by the image processing unit 55 and performs a control to display the endoscopic image on the display 15. The endoscopic image controlled to be displayed by the display control unit 56 is generated as a video signal to be displayed on the display 15 by the video signal generation unit 57 and is sent to the display 15. The display 15 displays the endoscopic image sent from the video signal generation unit 57 in accordance with the control of the display control unit 56.

The medical image processing device 17 acquires the endoscopic image generated by the image processing unit 55, and generates and outputs the diagnosis information and the reference information based on the endoscopic image. The medical image processing device 17 is a general-purpose PC provided with a processor and exhibits various functions through the installation of software. In the medical image processing device 17, similarly to the processor device 14, a program related to processing, such as image analysis processing, is also stored in a program memory (not shown). In the medical image processing device 17, the program within the program memory is operated by a central control unit (not shown) composed of an image processor, which is a second processor, or the like, whereby the functions of a medical image acquisition unit 81, a diagnosis information generation unit 82, a reference information generation unit 83, an information output unit 84, and a display control unit 85 are realized (see FIG. 7). In addition, the central control unit receives information from the processor device 14 or the like and controls each unit of the medical image processing device 17 based on the received information. Further, the central control unit is connected to a user interface, such as a keyboard (not shown), and also receives information, such as an instruction through the user interface.

The medical image processing device 17 is connected to the display 15 and performs a control of displaying various types of information generated by the medical image processing device 17. Various devices may be connected to the medical image processing device 17. Examples of the various devices include a user interface such as a keyboard for issuing an instruction, and a storage for storing data such as images and information. Additionally, the medical image processing device 17 has a network connection function for connection to the various devices. The medical image processing device 17 may be connected to, for example, a medical service support apparatus 630 (see FIG. 24) or the like using the network connection function.

Figure 7:
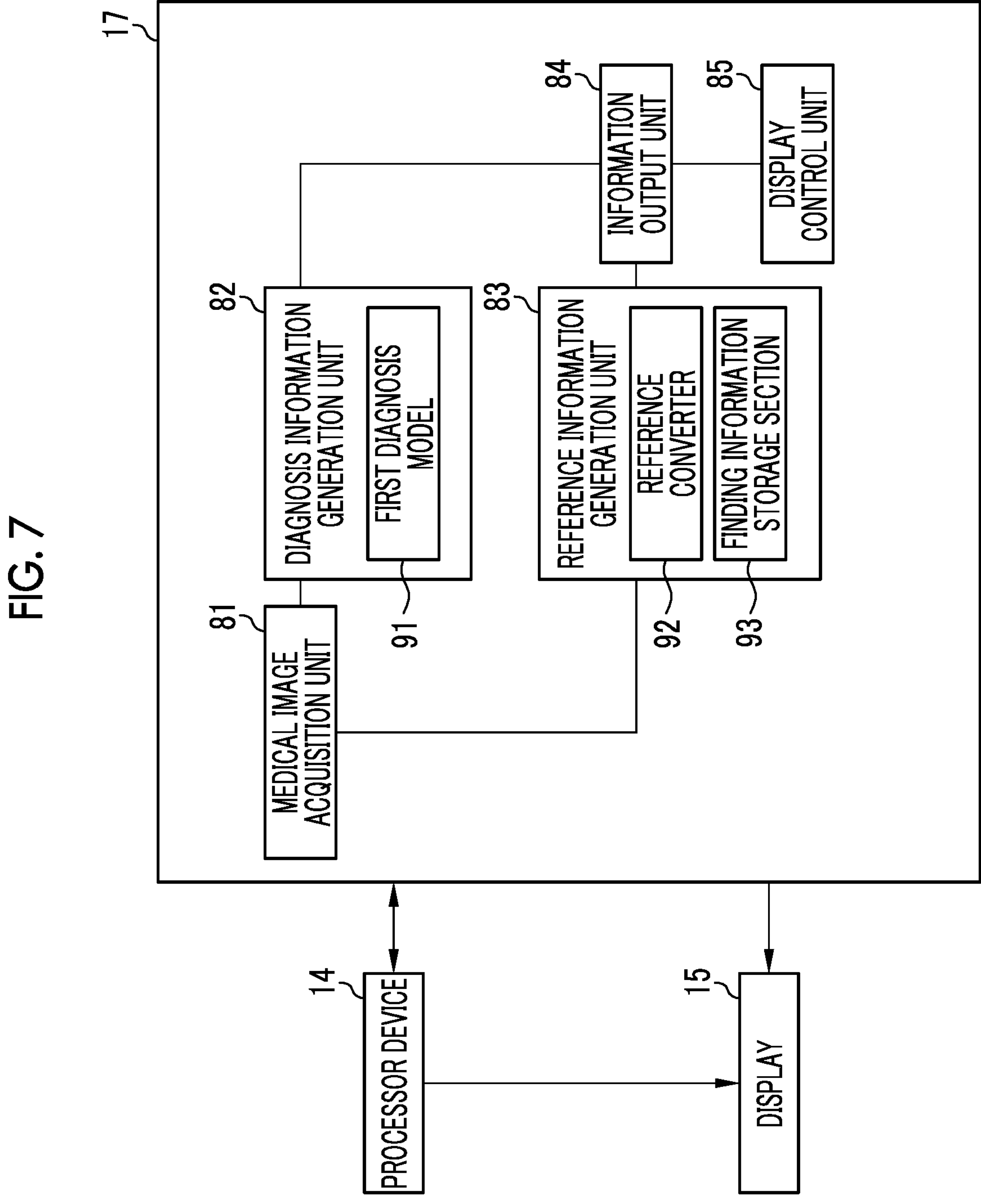
FIG. 7 is a block diagram showing a function of a medical image processing device.

As shown in FIG. 7, the medical image processing device 17 comprises the medical image acquisition unit 81, the diagnosis information generation unit 82, the reference information generation unit 83, the information output unit 84, and the display control unit 85. The medical image acquisition unit 81 acquires a plurality of types of endoscopic images sent from the processor device 14. The acquired endoscopic images are sent to the diagnosis information generation unit 82 and the reference information generation unit 83. The diagnosis information generation unit 82 comprises a first diagnosis model (first model) 91, and the reference information generation unit 83 comprises a reference converter 92 and a finding information storage section 93. The information output unit 84 receives the diagnosis information generated by the diagnosis information generation unit 82 and the diagnosis information reference information generated by the reference information generation unit 83 and outputs these pieces of information in order to store these pieces of information or notify a user such as a doctor. The display control unit 85 receives the diagnosis information and the reference information from the information output unit 84 and performs a control to display the diagnosis information and the reference information on the display 15.

In the present embodiment, the medical image acquisition unit 81 transmits the first image 72 among the plurality of types of imaged endoscopic images to the diagnosis information generation unit 82. The diagnosis information generation unit 82 generates the diagnosis information related to the diagnosis of the observation target shown in the endoscopic image in a case where the first image 72 sent from the medical image acquisition unit 81 is input. The diagnosis information generation unit 82 performs AI-based CAD as a method of acquiring the diagnosis information.

The diagnosis information indicates the severity or progression of various predicted diseases. In the diagnosis using the endoscopic image, various pieces of information related to the surface structure of the observation target, biological information of the mucosal surface layer, or the like are obtained from findings of the endoscopic image obtained through image-enhanced observation using image enhanced endoscopy (IEE). As the IEE, various methods are known such as a method of performing digital image processing on the endoscopic image obtained by imaging the observation target or a method of illuminating and imaging the observation target with specific illumination light.

With the endoscopic image obtained through the IEE, there is a probability that features on the image, which are different from those of the endoscopic image obtained from the normal image using white light, may be obtained or feature amounts may be obtained due to high resolution even with the same features as the normal image. Therefore, there is a probability that the severity or progression may be predicted using high accuracy by predicting and diagnosing the severity or progression based on the endoscopic image obtained through the IEE.

For example, IEE diagnostic techniques for predicting pathology using the IEE, such as various types of cancer, are doctor-driven in its construction. In the IEE diagnostic techniques, statistical relationships between the visual appearance obtained from the endoscopic image, that is, the structure of the blood vessel in the surface layer or mucous membrane of the observation target, and the pathology of the observation object, that is, the depth of cancer invasion, are found out, and in a case where the blood vessel or mucous membrane is in a predetermined state, classifications are defined for the pathology, that is, the extent of the depth of cancer. The classification of the depth of the cancer invasion of the observation target is diagnosis information. In this case, the classification of the structure of the blood vessel in the surface layer or mucous membrane of the observation target is reference information.

As the severity or progression, there exist, in addition to pathological severity and pathological progression determined by a pathologist or the like through observation of biopsy tissues, endoscopic severity and endoscopic progression determined by an endoscopist or the like through visual evaluation of endoscopic images. In the present specification, the accuracy in a case where the pathological severity or the pathological progression is predicted, or the like means a high ratio of coincidence between the result of the pathological severity or the pathological progression predicted based on the endoscopic image and actual pathological severity or pathological progression of the subject, and the accuracy in a case where the endoscopic severity or the endoscopic progression is predicted means a high ratio of coincidence between the result of the endoscopic severity or the endoscopic progression predicted based on the endoscopic image and actual endoscopic severity and endoscopic progression of the subject.

Specific examples of the IEE diagnostic techniques include vessel plus surface classification (VS classification) for diagnosing gastric cancer, the classification of the Japan Esophageal Society (IPCL classification) for diagnosing esophageal cancer, and JNET classification or NICE classification for diagnosing colorectal cancer.

For example, in VS classification, the diagnosis is performed by combining references (Regular, Irregular, and Absent) for microvascular architecture (V: microvascular (MV) architecture) and references (Regular, Irregular, and Absent) for a microsurface structure (S: microsurface (MS) structure) in endoscopic findings. For example, in a case where both V and S are classified as "Regular", a diagnosis is made that it is a hyperplastic polyp rather than cancer.

In addition, in the JNET classification, it is classified into four classifications, that is, Type 1, 2A, 2B, and 3, in each of the categories of Vessel pattern and Surface pattern in the endoscopic findings. Then, Type 1 is diagnosed as hyperplastic polyps, Type 2A is diagnosed as adenomas or low-grade carcinoma, Type 2B is diagnosed as high-grade carcinoma, and Type 3 is diagnosed as high-grade carcinoma in pathological findings.

In the present embodiment, the observation target is the large intestine, and the diagnosis information and the reference information regarding ulcerative colitis are acquired. The diagnosis information generation unit 82 uses the first image 72 acquired by performing the IEE through a method of illuminating and imaging the observation target with the first illumination light, which is specific illumination light, to perform the AI-based CAD, thereby generating the diagnosis information. The first image 72 is an endoscopic image obtained through the IEE, in which surface layer blood vessels and the like are enhanced. Using the first image 72 obtained by enhancing and imaging the surface layer blood vessels of the mucous membrane in the large intestine for the CAD may often lead to increased prediction accuracy of the endoscopic severity of ulcerative colitis. Therefore, the diagnosis information generation unit 82 can obtain the diagnosis information with high accuracy by using the first image 72.

The diagnosis information can be generated so as to correspond to various diagnostic techniques regardless of the classification in the IEE diagnostic technique. In the present embodiment, the classification is based on endoscopic findings of ulcerative colitis, and the diagnosis information and the reference information corresponding to Mayo score indicating the endoscopic severity are output. Therefore, as the diagnosis information, diagnosis information corresponding to the Mayo score is generated. The Mayo score is used to classify and diagnose the endoscopic severity into any of 0, 1, 2, or 3 according to each reference of endoscopic findings in the endoscopic findings for the normal image, and is widely used to evaluate the endoscopic severity of ulcerative colitis.

In the severity diagnosis of ulcerative colitis based on the Mayo score, erythema, visible vascular pattern, erosion, ulceration, or the like in endoscopic findings is used as a reference. In the endoscopic findings of the observation target, the severity is classified as a normal or inactive finding and corresponds to Mayo 0 in a case where the endoscopic finding does not correspond to "erythema, visible vascular pattern, erosion, or the like" in the reference, the severity is classified as mild and corresponds to Mayo 1 in a case where the endoscopic finding is "erythema, decreased vascular pattern, and mild bleeding tendency" in the reference, the severity is classified as moderate and corresponds to Mayo 2 in a case where the endoscopic finding is "marked erythema, loss of vascular pattern, bleeding tendency, and erosion" in the reference, and the severity is classified as severe and corresponds to Mayo 3 in a case where the endoscopic finding is "spontaneous bleeding and ulceration" in the reference. Therefore, the diagnosis information generation unit 82 generates any of Mayo 0, Mayo 1, Mayo 2, or Mayo 3 as the diagnosis information by using the first image 72.

The diagnosis information generation unit 82 outputs, based on one type of the plurality of types of endoscopic images, the diagnosis information regarding the diagnosis of the subject shown in the endoscopic image. Although any type of endoscopic image may be used, in the present embodiment, the diagnosis information generation unit 82 generates the diagnosis related to the endoscopic severity of ulcerative colitis based on the Mayo score as the diagnosis information by using the first image 72 obtained through the IEE. For example, information indicating that the endoscopic severity is "Mayo 2" in the endoscopic severity based on the Mayo score is the diagnosis information. Therefore, in the diagnosis, it is possible to generate the diagnosis information with high accuracy by using the first image 72 obtained through the IEE. Since this diagnosis information is the diagnosis information based on the endoscopic severity classification of the Mayo score, which is familiar to the doctor, it is possible to facilitate the doctor's understanding of the endoscopic severity.

Figures 8, 9:
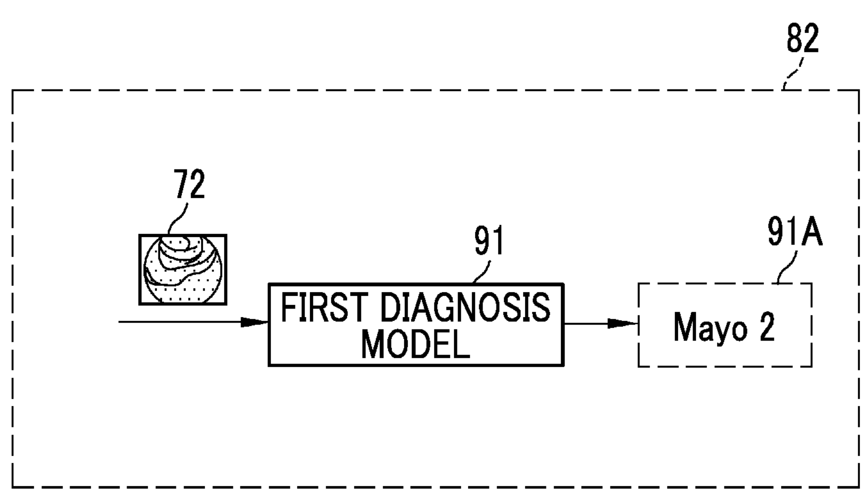
FIG. 8 is an explanatory diagram illustrating a function of a first diagnosis model.
FIG. 9 is an explanatory diagram illustrating finding information.

The diagnosis information generation unit 82 performs AI-based CAD using the first diagnosis model 91. Therefore, the first diagnosis model 91 is a learning model in machine learning. As shown in FIG. 8, as the first diagnosis model 91, a model that has been trained and adjusted to output diagnosis information 91A in response to an input of the first image 72, which is the endoscopic image, is used. In the present embodiment, the first diagnosis model 91 receives an input of the first image 72 obtained by imaging the observation target in the large intestine and outputs the diagnosis related to the endoscopic severity in the Mayo score of ulcerative colitis as the diagnosis information 91A such as "Mayo 2", for example. Therefore, before the diagnosis, the first image 72 with a pre-assigned diagnosis result of ulcerative colitis can be used as training data.

Since there is a probability of obtaining the diagnosis information 91A with higher accuracy, the first diagnosis model 91 is preferably a multi-layer neural network model. From the fact that it is a learning model that receives an input of the endoscopic image and outputs the diagnosis information 91A, the learning model may be a convolutional neural network model or a deep learning model. Further, it is preferable that the first diagnosis model 91 has a layered structure comprising a first output layer that outputs the diagnosis information and at least one first intermediate layer. The first diagnosis model 91 can employ various techniques in machine learning in order to output the diagnosis information 91A with high accuracy in a case of outputting the diagnosis information 91A in response to an input of the first image 72, which is the endoscopic image.

The reference information generation unit 83 generates the reference information regarding the reference for the diagnosis of the diagnosis information 91A generated by the diagnosis information generation unit 82 in a case where a medical image showing the same subject as the subject shown in the first image 72 is input. The medical image showing the same subject means that the subject shown in the medical image does not need to be exactly the same and at least a part of the subject shown in one medical image is shown in the other medical image. That is, in a case where a part of the subject is commonly included in a plurality of medical images, these medical images are medical images showing the same subject. The reference information is information regarding the reference for the diagnosis performed by the diagnosis information generation unit 82. The diagnosis information generation unit 82 generates the diagnosis information 91A through the CAD, but does not generate information regarding the reference for the diagnosis. Therefore, the reference information regarding the diagnosis performed by the diagnosis information generation unit 82 is generated by the reference information generation unit 83.

The reference information is a reference in a case where the diagnosis information generation unit 82 acquires the diagnosis information 91A regarding the diagnosis of the subject shown in the first image 72 based on the first image 72. In a case where the diagnosis information generation unit 82 generates and acquires the endoscopic severity based on the Mayo score as the diagnosis information 91A, the reference information is a finding for determining the Mayo score, and specifically, is information regarding erythema, loss of vascular pattern, erosion, ulceration, or the like. In the Mayo score, the severity is determined based on the degree of these findings as the reference. In the present embodiment, in order to perform the endoscopic severity diagnosis of ulcerative colitis in the diagnosis information generation unit 82, the reference information generation unit 83 generates the reference information regarding the references of erythema, loss of vascular pattern, and ulceration in the Mayo score.

The reference information generation unit 83 generates the reference information regarding the reference for the diagnosis of the diagnosis information 91A by using the medical image showing the same subject as the subject shown in the first image 72 and the reference converter 92. The reference converter 92 is created in advance before the diagnosis and is created using assigned reference information which is the reference information assigned to the normal image 71 (second medical image). The endoscopic image to which the assigned reference information is assigned is the endoscopic image acquired by the medical image acquisition unit 81 and is an endoscopic image having a type different from that of the first image 72. In the present embodiment, since the types of the endoscopic image are distinguished based on the spectrum of illumination light, the first image 72 acquired with the first illumination light and the normal image 71 acquired with the normal light are endoscopic images different from each other.

In order to create the reference converter 92 in advance before the diagnosis, the assigned reference information is acquired in advance before the diagnosis. Information in which the assigned reference information is assigned to the normal image 71 acquired in advance before the diagnosis is used as finding information, and the finding information is stored in the finding information storage section 93. The reference converter 92 is created using the finding information stored in the finding information storage section 93.

In the present embodiment, the reference information is information on erythema, loss of vascular pattern, and ulceration, which are findings for determining the Mayo score. Therefore, information in which the information on these references is assigned to the normal image 71 is used as the assigned reference information. The assigned reference information can be the doctor's findings for the normal image 71. That is, the doctor assigns the degree of the finding as a sub-score by visually observing the normal image 71.

As shown in FIG. 9, finding information 94 is information obtained by the doctor through evaluation for erythema, loss of vascular pattern, and ulceration and assignment of evaluation values within a range of 0 to 4 with a minimum value of 0 and a maximum value of 4, based on the normal image 71. The finding information 94 includes a result of the diagnosis of endoscopic severity by the doctor based on the normal image 71. For example, in the image number "W000001", the finding information 94 describes that the field of "erythema" is "1", the field of "visible vascular pattern" is "0", the field of "ulceration" is "0", and the field of "endoscopic severity" is "Mayo 1", and the doctor's findings for the subject shown in the normal image 71 with the image number "W000001" are recorded that erythema is level 1, loss of vascular pattern is level 0, ulceration is level 0, and the endoscopic severity is Mayo 1. The type of endoscopic images with image numbers starting with W is the normal image 71.

Next, the endoscopic image showing the same subject as the subject shown in the normal image 71 having the assigned reference information is prepared. A feature amount for outputting the reference information is acquired from this endoscopic image by using machine learning or the like. The reference converter 92 that converts the feature amount into the reference information is created by using the feature amount and the assigned reference information. With the reference converter 92, the feature amount acquired from the endoscopic image showing the same subject as the subject shown in the normal image 71 having the assigned reference information can be output by being converted into the same items and values as the sub-scores of the Mayo score, such as the finding information 94. One or a plurality of feature amounts are acquired. Since the feature amount is converted to obtain the reference information, it is preferable that there are a plurality of feature amounts in a case where there are a plurality of pieces of reference information.

The endoscopic image showing the same subject as the subject shown in the normal image 71 having the assigned reference information can be, for example, a medical image with an imaging time close to the imaging time of the normal image 71. It is preferable that the endoscopic image showing the same subject as the subject shown in the normal image 71 having the assigned reference information has a close imaging time to the extent that the plurality of endoscopic images showing the same subject as the normal image 71 are obtained. For example, in a case where the number of frames is 60 frames per second (fps), it is considered that the endoscopic images acquired in consecutive frames almost reliably show the same subject.

Figure 10:
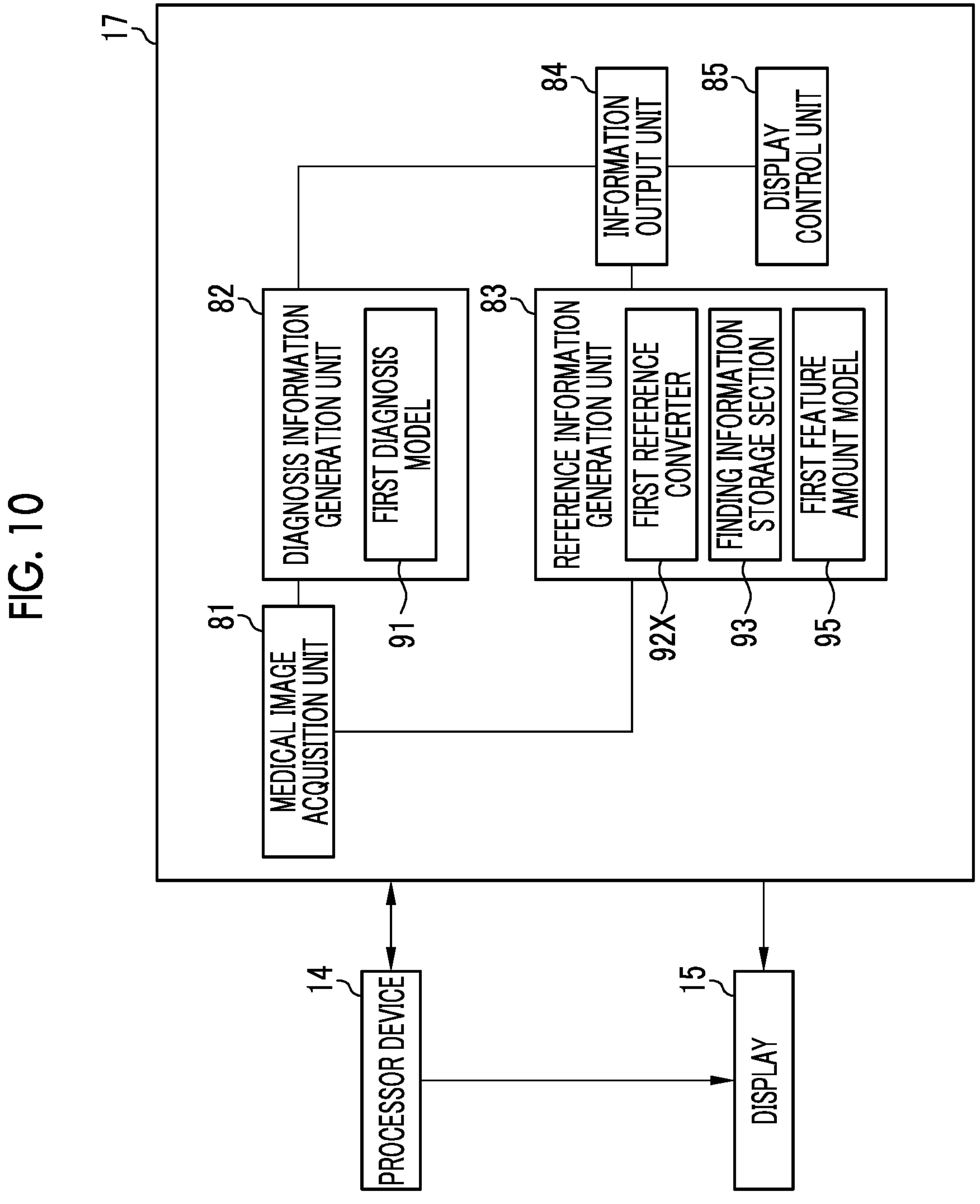
FIG. 10 is a block diagram showing a function of the medical image processing device in which a reference information generation unit comprises a first feature amount model.

As shown in FIG. 10, in a case where the feature amount for obtaining the reference information is obtained by using the endoscopic image showing the same subject as the subject shown in the normal image 71 used in the finding information 94, the reference information generation unit 83 may comprise a first reference converter 92X and a first feature amount model 95. In a case where the first diagnosis model is a first model, the first feature amount model and a second feature amount model, which will be described below, are second models different from the first model.

It is preferable that the first feature amount model 95 is a learning model in machine learning, which receives an input of the endoscopic image and outputs the feature amount.

Figure 11:
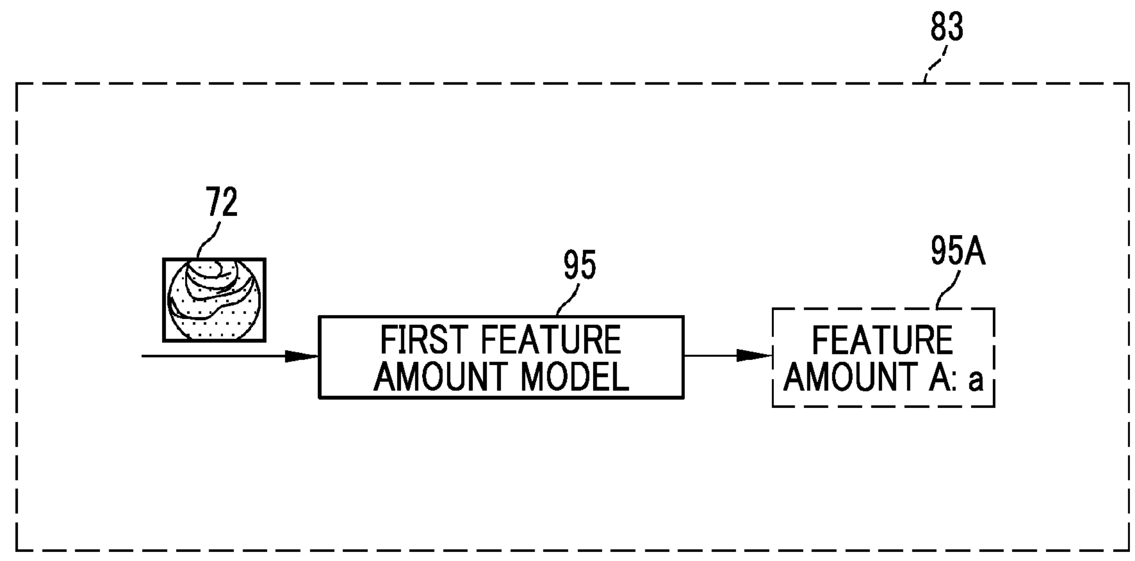
FIG. 11 is an explanatory diagram illustrating a function of the first feature amount model.

As shown in FIG. 11, as the first feature amount model 95, a model that has been trained and adjusted to output the feature amount, such as a feature amount A, as a numerical value, such as a, in response to an input of the first image 72, which is the endoscopic image, is used. It is preferable that the first feature amount model 95 is a multi-layer neural network model. From the fact that it is a learning model that receives an input of the endoscopic image and outputs the feature amount, the learning model may be a convolutional neural network model or a deep learning model. Further, it is preferable that the first feature amount model 95 has a layered structure comprising a second output layer that outputs the feature amount and at least one second intermediate layer.

In the present embodiment, since it is preferable that the first feature amount model 95 receives an input of the first image 72 showing the same subject as the subject appearing in the normal image 71 having the assigned reference information and outputs the feature amount related to the sub-score such as erythema which is the reference in the Mayo score of ulcerative colitis, the first image 72 with a pre-assigned sub-score such as erythema, which is the reference of ulcerative colitis, before the diagnosis can be used as training data.

As the feature amount output by the first feature amount model 95, it is preferable that the feature amount having a high correlation with the reference information can be acquired without limitation. Since the feature amount can be effectively selected in a case where a large amount of feature amounts exist, it is preferable that the first feature amount model 95 acquires the feature amount from the intermediate layer as an autoencoder or acquires the feature amount through clustering. As described above, the first feature amount model 95 can employ various techniques in machine learning in order to acquire the feature amount that has a high correlation with the reference information and is easy to select in a case of acquiring the feature amount in response to an input of the first image 72, which is the endoscopic image.

As shown in FIG. 12, the feature amount output by the first feature amount model 95 can be recorded as converter information 96 in combination with the finding information 94. In the converter information 96, an image with the image number starting with B is the first image 72. The first image 72 with the image number B000001 is an endoscopic image showing the same subject as the subject in the normal image 71 with the common digits of the image number, such as the image number W000001. Since three types of feature amounts, that is, the feature amount A, the feature amount B, and the feature amount C, are acquired, the converter information 96 indicates the feature amount A in the field of "A", the feature amount B in the field of "B", and the feature amount C in the field of "C". The feature amounts each have been adjusted to be represented with a maximum value of 100 and a minimum value of 0.

For example, in the image number "B000001", the converter information 96 describes that the field of "A" of the feature amount is "11", the field of "B" is "5", and the field of "C" is "0", which indicates that the feature amounts output by the first feature amount model 95 based on the first image 72 with the image number B000001 is 11 for the feature amount A, 5 for the feature amount B, and 0 for the feature amount C. The endoscopic images with the image number B000001 and the like are acquired in a frame immediately before the normal image 71 with W000001, which is a different type of endoscopic image, from the digits of the image numbers, and include the same subject.

The feature amount and the assigned reference information acquired based on the endoscopic image showing the same subject as the subject shown in the normal image 71 having the assigned reference information are used to create the first reference converter 92X that converts the feature amount into the reference information. The first reference converter 92X can be created by performing a regression analysis on the feature amount and each piece of the assigned reference information to associate both of them with each other.

The regression analysis may be performed on each piece of the assigned reference information and the feature amount such that one piece of the assigned reference information corresponds to one feature amount most correlated with the one piece of the assigned reference information, but for the better correlation, it is preferable that a plurality of feature amounts are acquired and then the regression analysis is performed such that one piece of the assigned reference information corresponds to the plurality of feature amounts. As the regression analysis, any method need only be used as long as the two can be associated with each other with a good correlation, and a known mathematical method or a machine learning technique such as a support vector machine can be used.

As shown in FIG. 13, the normal image 71 and the first image 72 showing the same subject are used. From the first image 72, a first feature amount 95A, that is, "feature amount A: a", "feature amount B: b", and "feature amount C: c", is acquired for three types of different feature amounts from the feature amount A to C through the first feature amount model 95. Here, a, b, and c are digits or the like indicating an amount. Meanwhile, the normal image 71 is used to assign scores to the references for "erythema", "loss of vascular pattern", and "ulceration", which are sub-scores of the Mayo score obtained through visual observation of the doctor, such as "erythema: 2", "loss of vascular pattern: 0", and "ulceration: 1", respectively, thereby obtaining assigned reference information 94A. The regression analysis is performed on three types of values, that is, "feature amount A: a", "feature amount B: b", and "feature amount C: c", and for example, the value of "erythema: 2" which is the reference information. Through the regression analysis, a function for converting three types of values, that is, the feature amount A, the feature amount B, and the feature amount C, into a value of "erythema" of the reference information is obtained. This function is stored in the reference converter 92. The value of "erythema" of the reference information calculated and generated using this function can be used as the sub-score of the Mayo score.

A plurality of the first reference converters 92X may be generated for each piece of the reference information. In the present embodiment, a first reference converter A 92A that converts three types of values, that is, the feature amount A, the feature amount B, and the feature amount C, into the value of "erythema" of the reference information, a first reference converter B 92B that converts three types of values, that is, the feature amount A, the feature amount B, and the feature amount C, into the value of "visible vascular pattern" of the reference information, and a first reference converter C 92C that converts three types of values, that is, the feature amount A, the feature amount B, and the feature amount C, into the value of "ulceration" of the reference information are provided.

As described above, the diagnosis information generation unit 82 and the reference information generation unit 83 are generated in advance before the diagnosis. After that, the diagnosis support observation mode is operated during the diagnosis, and the normal image 71 and the first image 72 are captured during the diagnosis. In a case where the first image 72 is input to the diagnosis information generation unit 82 and the reference information generation unit 83, the diagnosis information 91A is output from the diagnosis information generation unit 82, and the reference information is output from the reference information generation unit 83.

Figure 14:
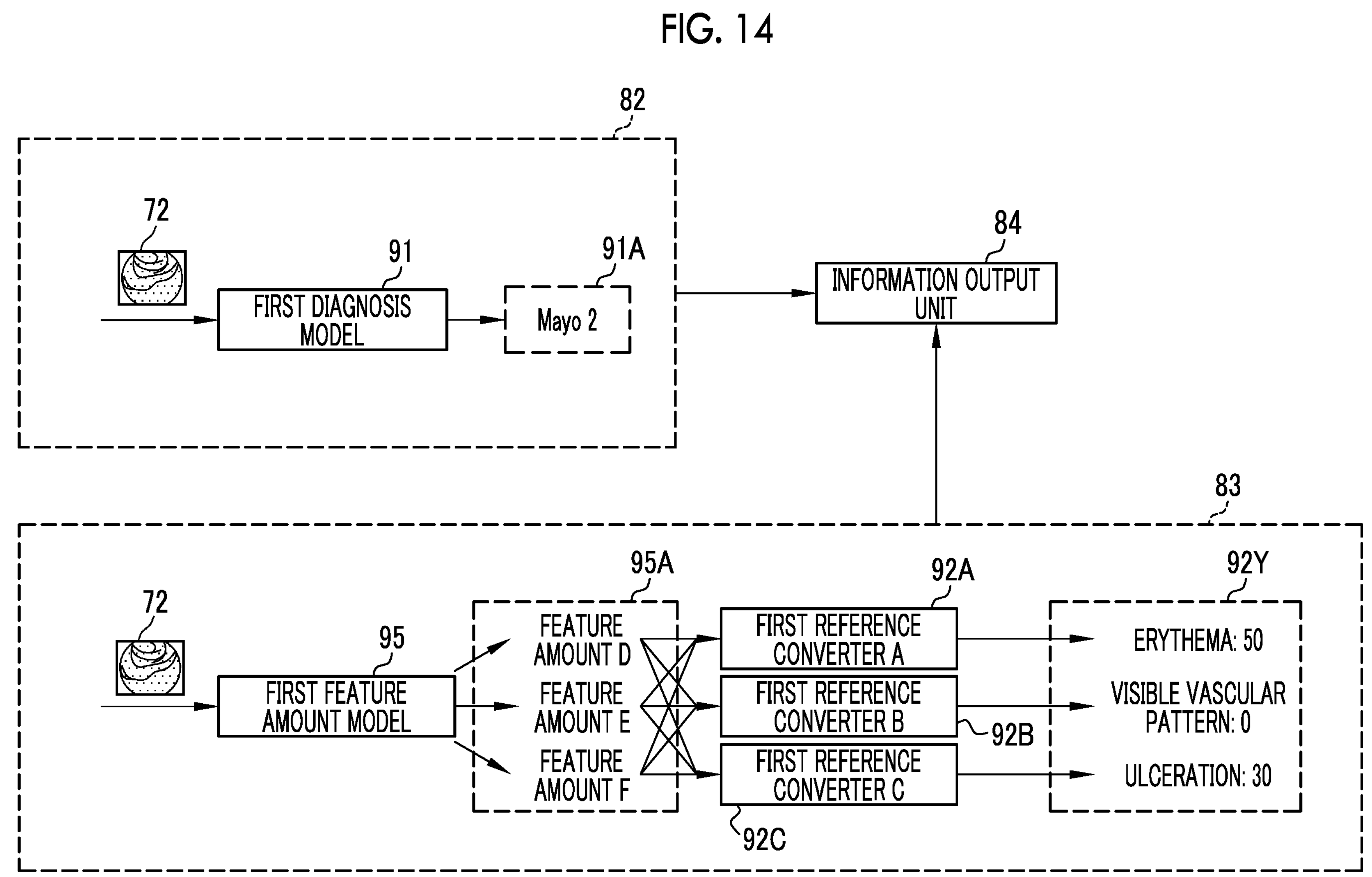
FIG. 14 is an explanatory diagram illustrating a generation method of diagnosis information and reference information.

In the diagnosis support observation mode, the information output unit 84 receives the diagnosis information 91A from the diagnosis information generation unit 82, receives the reference information from the reference information generation unit 83, and outputs these in association with each other. As shown in FIG. 14, the diagnosis information 91A is obtained by sending the first image 72 to the diagnosis information generation unit 82 and inputting the first image 72 to the first diagnosis model 91.

The diagnosis information is, for example, "Mayo 2", which is the diagnosis result of the Mayo score, or the like. Reference information 92Y is generated by sending the same first image 72 as the image sent to the diagnosis information generation unit 82 to the reference information generation unit 83 and inputting the first image 72 to the first feature amount model 95 to acquire the feature amount. Three types of feature amounts, that is, a feature amount D, a feature amount E, and a feature amount F, are acquired, and these feature amounts are input to the first reference converter A 92A, the first reference converter B 92B, and the first reference converter C 92C and converted into the reference information 92Y of the references, that is, "erythema", "loss of vascular pattern", and "ulceration", respectively. The reference information 92Y is output with scores such as "erythema: 50", "visible vascular pattern: 0", and "ulceration: 30". The information output unit 84 outputs the diagnosis information 91A and the reference information 92Y in association with each other. An output destination can be the display 15, a recording device (not shown), or the like.

Figure 15:
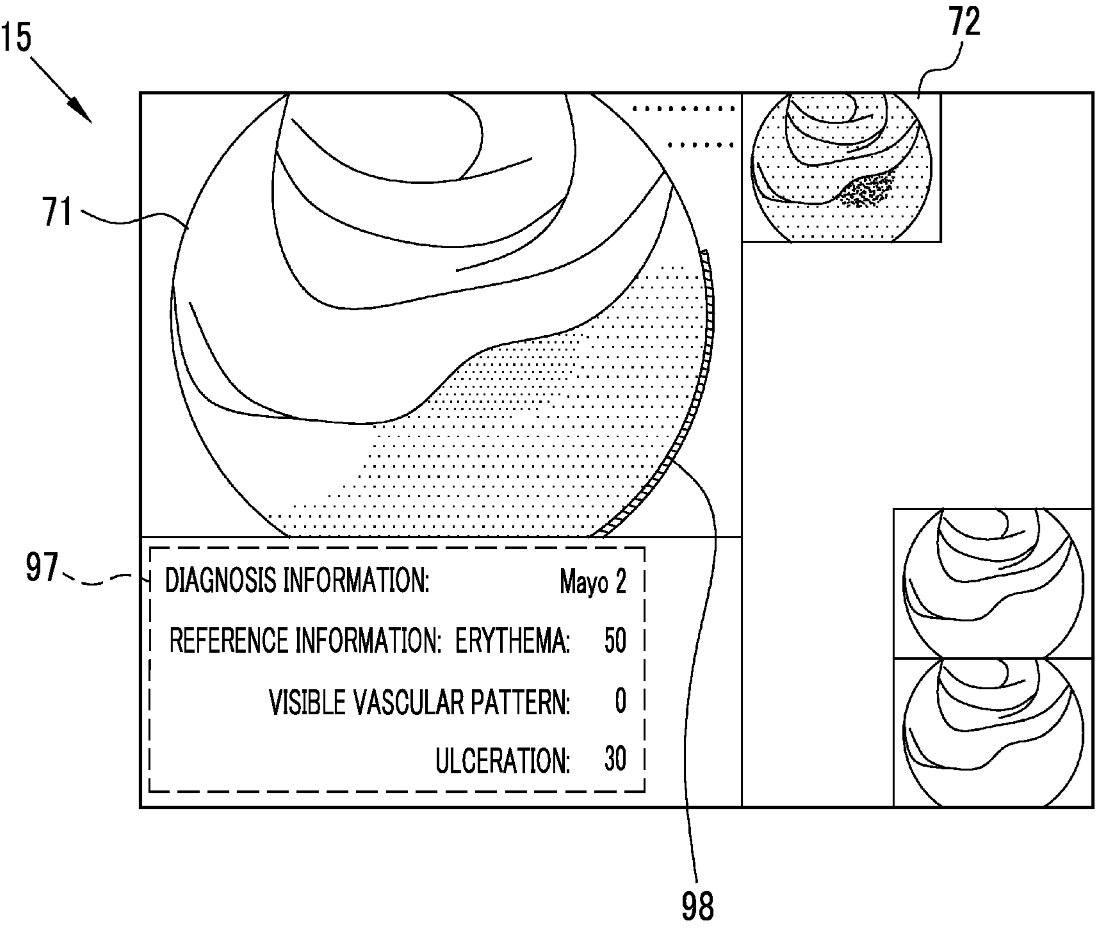
FIG. 15 is an image diagram in which the diagnosis information and the reference information are displayed on a display.

In the diagnosis support observation mode, the information output unit 84 sends the diagnosis information 91A and the reference information 92Y to the display control unit 85. The display control unit 85 performs a control of displaying the diagnosis information 91A and the reference information 92Y on the display 15 by creating a screen for displaying the diagnosis information 91A and the reference information 92Y and, for example, disposing the screen at a predetermined position. As shown in FIG. 15, on the display 15, the normal image 71, which is captured in the frame following the frame in which the first image 72 which is the endoscopic image used by the medical image processing device 17 is captured, and diagnosis information and reference information 97 are displayed as "diagnosis information: Mayo 2", and "reference information: erythema: 50, visible vascular pattern: 0, ulceration: 30". In addition, in a case where the normal image 71 is displayed on the display 15, a combination of the medical image processing device 17 and CAD indicating a lesion portion may be used to indicate the lesion portion through a lesion region indicator 98 generated using the CAD indicating the lesion portion. As described above, through a glance at the display 15, the doctor can proceed with the endoscopic examination by referring to the natural color normal image 71 that is easy for the human being to see, the diagnosis result, the numerical values of the diagnosis reference, and the like of the Mayo score calculated by the medical image processing device 17 on the subject appearing in the normal image 71.

Figure 16:
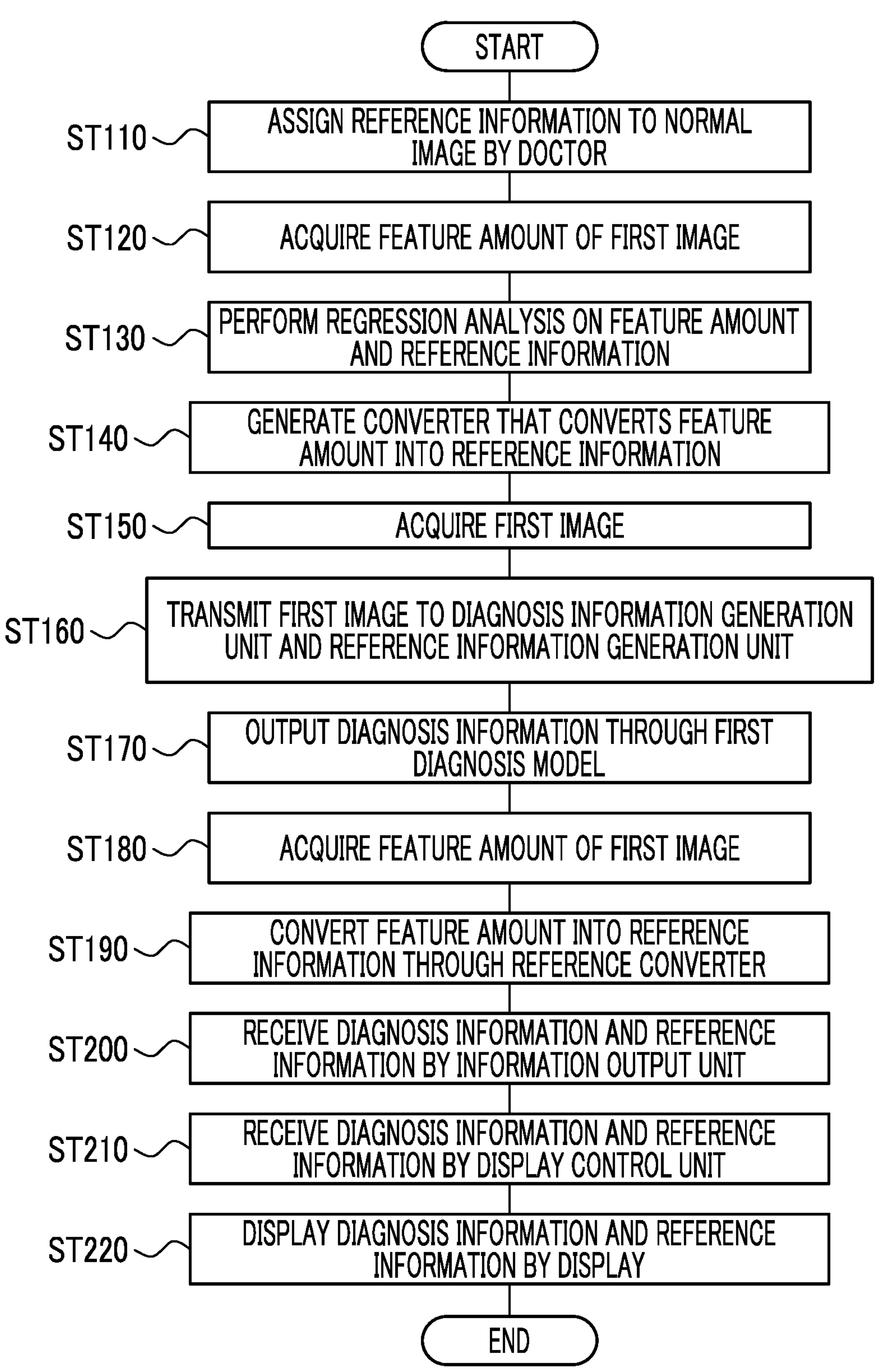
FIG. 16 is a flowchart showing a series of flows in which the diagnosis information and the reference information are displayed in the medical image processing device.

A series of flows of endoscopic image processing of the present embodiment by the medical image processing device 17 will be described with reference to a flowchart of FIG. 16. First, the first reference converter 92X is generated. For this purpose, the first image 72 and the normal image 71, which are consecutively captured, are prepared, and the doctor assigns the reference information 92Y to the normal image 71 (step ST110). The first image 72 and the normal image 71 are endoscopic images showing the same subject. The reference information 92Y is three types of references, that is, "erythema", "loss of vascular pattern", and "ulceration", which are sub-scores of the Mayo score. The assigned reference information 94A, which is the assigned reference information 92Y, and the like are stored in the finding information storage section 93.

In the reference information generation unit 83, the first image 72 is input to the first feature amount model 95, and three types of feature amounts, that is, the feature amount A, the feature amount B, and the feature amount C, are obtained (step ST120). The three types of feature amounts are stored in the finding information storage section 93, and the regression analysis for associating the three types of feature amounts with one piece of the reference information 92Y is performed (step ST130). As described above, the first reference converter 92X that converts the three types of feature amounts into one piece of the reference information 92Y is generated. Since the first reference converter 92X is generated for each piece of the reference information 92Y, three types of first reference converters 92, that is, the first reference converter A 92A that converts the three types of feature amounts into the reference of "erythema", the first reference converter B 92B that converts the three types of feature amounts into the reference of "visible vascular pattern", and the first reference converter C 92C that converts the three types of feature amounts into the reference of "ulceration", are generated (step ST140).

Next, through the diagnosis support observation mode, the endoscopic examination is started, and the first image 72 is acquired (step ST150). The medical image acquisition unit 81 receives the first image 72 and transmits the first image 72 to the diagnosis information generation unit 82 and the reference information generation unit 83 (step ST160). In the diagnosis information generation unit 82, the first diagnosis model 91 outputs the diagnosis information 91A in response to an input of the first image 72 (step ST170). In the reference information generation unit 83, three types of feature amounts, that is, the feature amount D, the feature amount E, and the feature amount F, are obtained by the first feature amount model 95 through an input of the first image 72 (step ST180). The three types of feature amounts, that is, the feature amount D, the feature amount E, and the feature amount F, are input to each of the first reference converter A 92A, the first reference converter B 92B, and the first reference converter C 92C, whereby the value of "erythema", which is the sub-score of the Mayo score, is output from the first reference converter A 92A, the value of "visible vascular pattern" is output from the first reference converter B 92B in the same manner, and the value of "ulceration" is output from the first reference converter C 92C in the same manner, as the reference information 92Y (step ST190).

The output diagnosis information and reference information 97 are received by the information output unit 84 (step ST200). The information output unit 84 outputs the diagnosis information and reference information 97 in association with each other to the display control unit 85 (step ST210). The display control unit 85 performs a control to display the diagnosis information and reference information 97 on the display 15. The display 15 displays the normal image 71 acquired through the endoscopic examination, and the diagnosis information and reference information 97 output by the medical image processing device 17 for the subject shown in the normal image 71 (step ST220).

As described above, the medical image processing device 17 uses the endoscopic image obtained through the IEE to obtain highly accurate diagnosis information that cannot be obtained only from the normal image 71, for the purpose of obtaining the diagnosis information 91A. Meanwhile, the medical image processing device 17 obtains the reference information associated with the normal image 71 using the normal light, which is normally familiar to the doctor, even by using the endoscopic image obtained through the IEE, for the purpose of obtaining the reference information 92Y. Therefore, both high diagnosis accuracy and high interpretability with respect to the diagnosis result can be obtained. Further, in the first reference converter 92X, in a case where a configuration is employed in which one piece of the reference information 92Y is converted by using a plurality of feature amounts, the reference information 92Y with more excellent accuracy can be obtained.

The diagnosis information generation unit 82 may acquire the first feature amount 95A of the first image 72, and may acquire the diagnosis information 91A based on the first feature amount 95A. Since the diagnosis information generation unit 82 generates the diagnosis information 91A of the first image 72 through the first diagnosis model 91, the first feature amount 95A may be generated in the first diagnosis model 91.

The first diagnosis model 91 that generates the first feature amount 95A need only be a model that can acquire the first feature amount 95A, and examples thereof include a model that can acquire the first feature amount 95A from the intermediate layer of the first diagnosis model 91. Since the first feature amount 95A can be appropriately acquired, a model similar to the first feature amount model 95 can be employed. Further, since the feature amount can be effectively selected in a case where a large amount of feature amounts exist, it is preferable that the first diagnosis model 91 acquires the feature amount from the intermediate layer as an autoencoder or acquires the feature amount through clustering. The first diagnosis model 91 can employ various techniques in machine learning in order to output the diagnosis information 91A with high accuracy and acquire the feature amount that is easy to select in a case of acquiring the diagnosis information 91A in response to an input of the first image 72, which is the endoscopic image.

Further, in a case where the first diagnosis model 91 generates the first feature amount 95A, the reference information 92Y may be acquired by generating the reference converter 92 using the assigned reference information 94A and the first image 72 showing the same subject as the subject shown in the normal image 71 to which the assigned reference information 94A is assigned, acquiring the first feature amount 95A through the reference information generation unit 83, and converting the first feature amount 95A through the reference converter 92.

Figure 17:
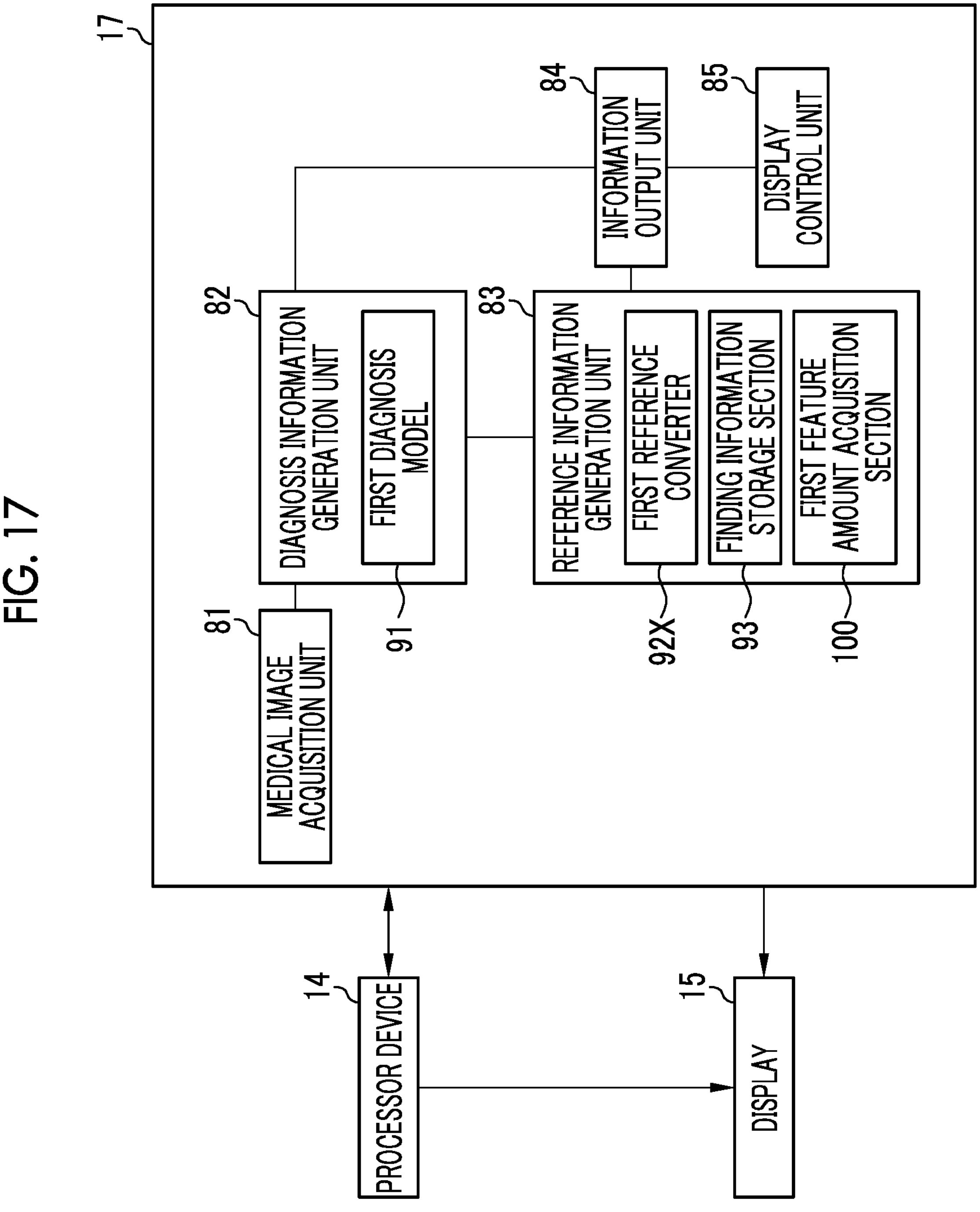
FIG. 17 is a block diagram showing a function of the medical image processing device in which the reference information generation unit comprises a first feature amount acquisition section.

As shown in FIG. 17, in this case, the reference information generation unit 83 comprises a first feature amount acquisition section 100, and the first feature amount acquisition section 100 acquires the feature amount generated by the first diagnosis model 91. A plurality of feature amounts may be generated by the first diagnosis model 91. The reference converter 92 converts one or a plurality of feature amounts acquired from the first diagnosis model 91 into the reference information 92Y.

Figure 18:
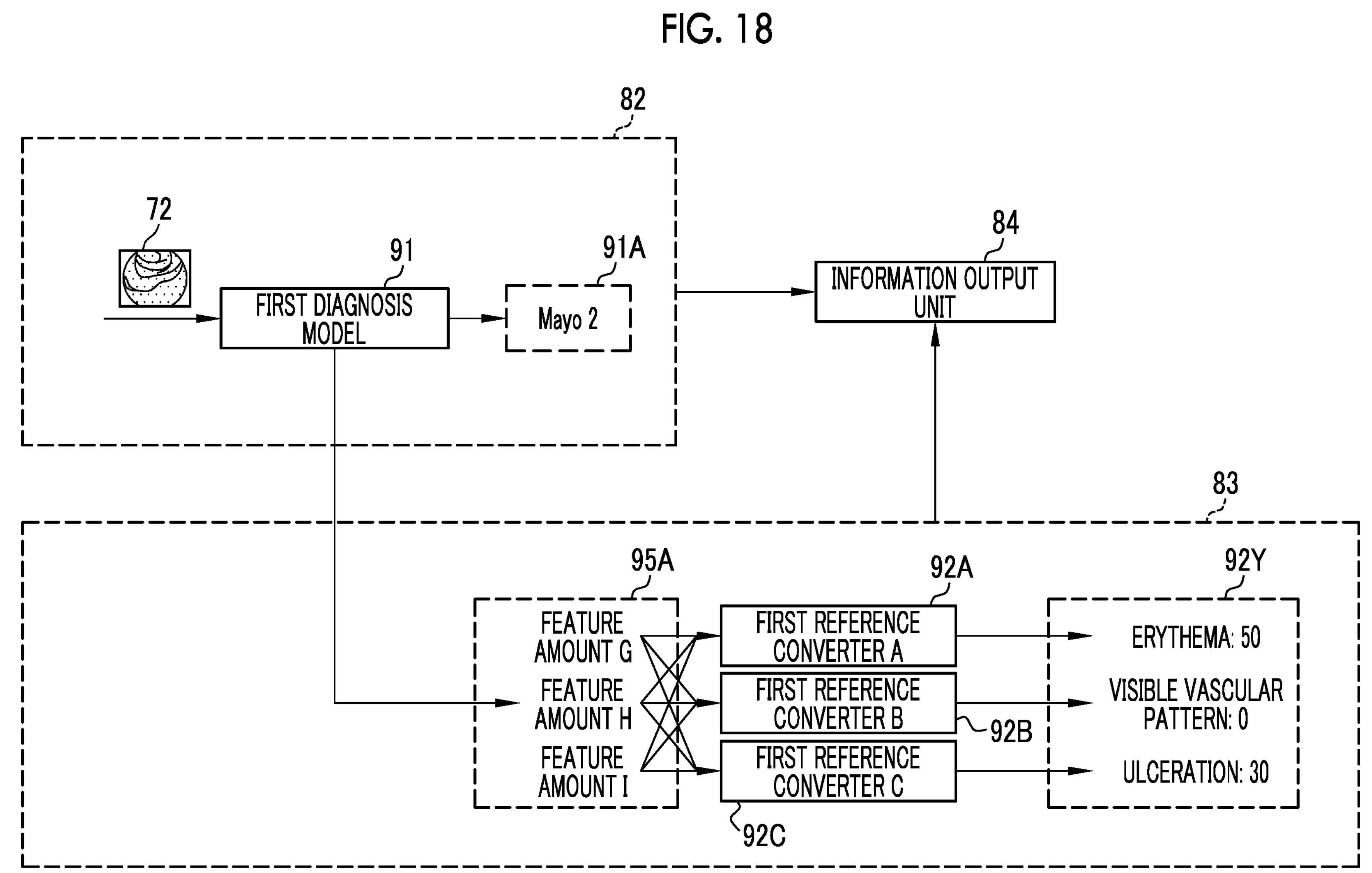
FIG. 18 is an explanatory diagram illustrating a flow of a first feature amount.

As shown in FIG. 18, the first diagnosis model 91 outputs the diagnosis information 91A based on the first image 72 and, in this case, generates the first feature amount 95A. For example, the first diagnosis model 91 has a first output layer that outputs the diagnosis information 91A and the first intermediate layer, and the first intermediate layer is disposed before the first output layer and calculates the first feature amount 95A. The first output layer outputs the diagnosis information 91A based on the first feature amount 95A. In the present embodiment, in the first diagnosis model 91, three types of feature amounts, that is, a feature amount G, a feature amount H, and a feature amount I, are generated as the first feature amount 95A.

In a case where the first feature amount model 95 has a layered structure comprising a second output layer that outputs the feature amount and at least one second intermediate layer, and the first diagnosis model 91 has a layered structure comprising the first output layer that outputs the feature amount and at least one first intermediate layer, the second intermediate layer may share the first intermediate layer. Even with such a method, the first feature amount model 95 can generate the three types of feature amounts, that is, the feature amount G, the feature amount H, and the feature amount I.

The reference information generation unit 83 inputs the feature amount G, the feature amount H, and the feature amount I, which are acquired by the first feature amount acquisition section 100, to each of the first reference converter A 92A, the first reference converter B 92B, and the first reference converter C 92C, to convert the feature amounts to three types of reference information 92Y In the same manner as described above, as the reference information 92Y, the value of "erythema" of the sub-score in the Mayo score is generated from the first reference converter A 92A, the value of "visible vascular pattern" is generated from the first reference converter B 92B in the same manner, and the value of "ulceration" is generated from the first reference converter C 92C in the same manner.

Figure 19:
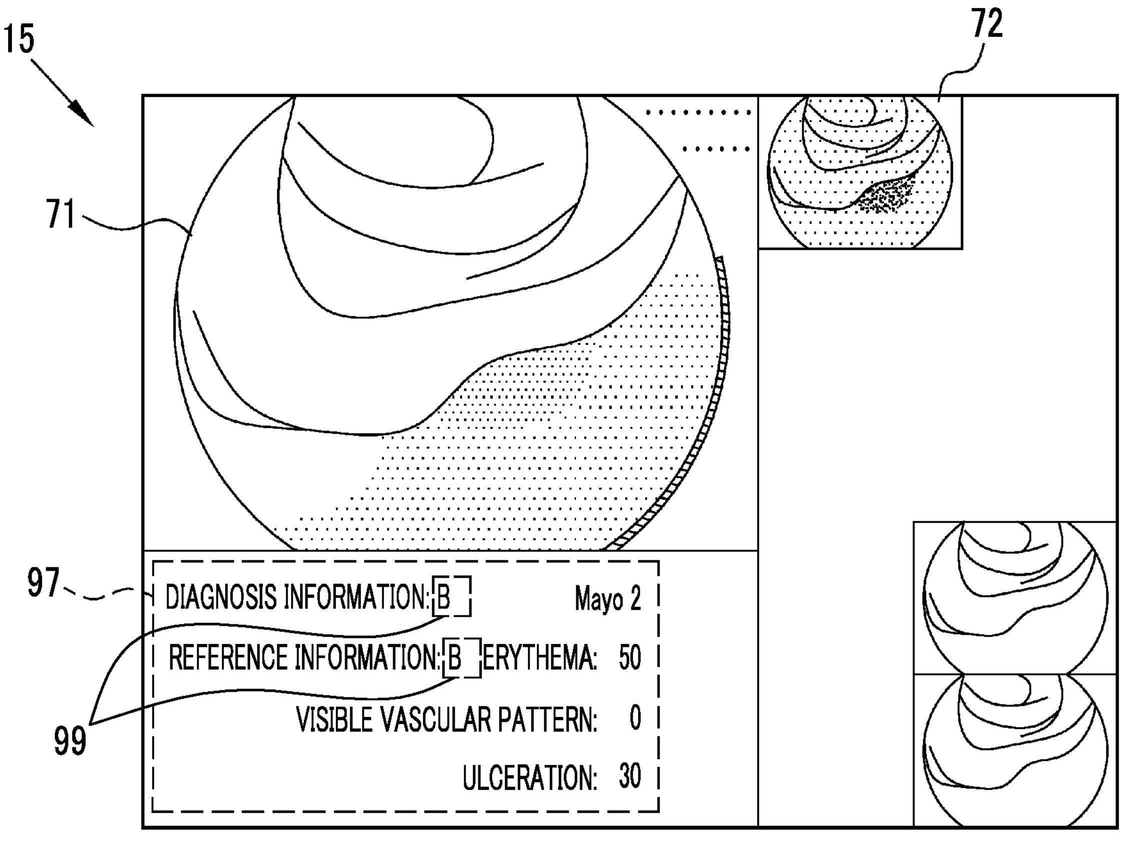
FIG. 19 is an image diagram in which the diagnosis information and the reference information are displayed on the display with a type of an image used added.

Further, in the same manner as described above, the diagnosis information and reference information 97 are sent to the information output unit 84 and displayed on the display 15 by the display control unit 85. As shown in FIG. 19, which type of endoscopic image is input to the CAD to obtain the diagnosis information 91A or the reference information 92Y may be indicated by a rationale image indicator 99. For example, a case where the rationale image indicator 99 is indicated as "B" indicates that the value is obtained through the CAD using the first image 72. In the present embodiment, since both the diagnosis information and reference information 97 are acquired through the CAD using the first image 72, "B" is displayed. In a case where the value is obtained through the CAD using the input normal image 71, the rationale image indicator 99 is indicated as "W".

As described above, in the diagnosis information generation unit 82, the first diagnosis model 91 acquires the first feature amount 95A based on the first image 72, whereby the reference information generation unit 83 can acquire the reference information 92Y by utilizing the first feature amount 95A generated by the first diagnosis model 91. Therefore, it is preferable particularly in terms of saving calculation resources because the first feature amount 95A can be obtained through a single calculation. Further, since the reference information generation unit 83 acquires the reference information 92Y by using the first feature amount 95A acquired by the first diagnosis model 91 based on the first image 72, the diagnosis information 91A and the reference information 92Y are associated with each other, and the reference information 92Y can be regarded as a diagnosis rationale of the diagnosis information 91A.

In the diagnosis support observation mode, the reference information generation unit 83 may acquire the feature amount (hereinafter, referred to as a second feature amount) of the normal image 71 (second medical image) to generate the reference information 92Y obtained through the conversion of the second feature amount by a second reference converter 120 that converts the second feature amount into the reference information 92Y In this case, the second reference converter 120 is generated by using the assigned reference information 94A and the normal image 71. The reference information generation unit 83 generates the second feature amount of the normal image 71 showing the same subject as the subject shown in the first image 72, and generates the reference information 92Y by converting the second feature amount into the reference information 92Y through the second reference converter 120. The normal image 71 from which the second feature amount is acquired and the first image 72 from which the diagnosis information 91A is acquired are endoscopic images showing the same subject.

Figure 20:
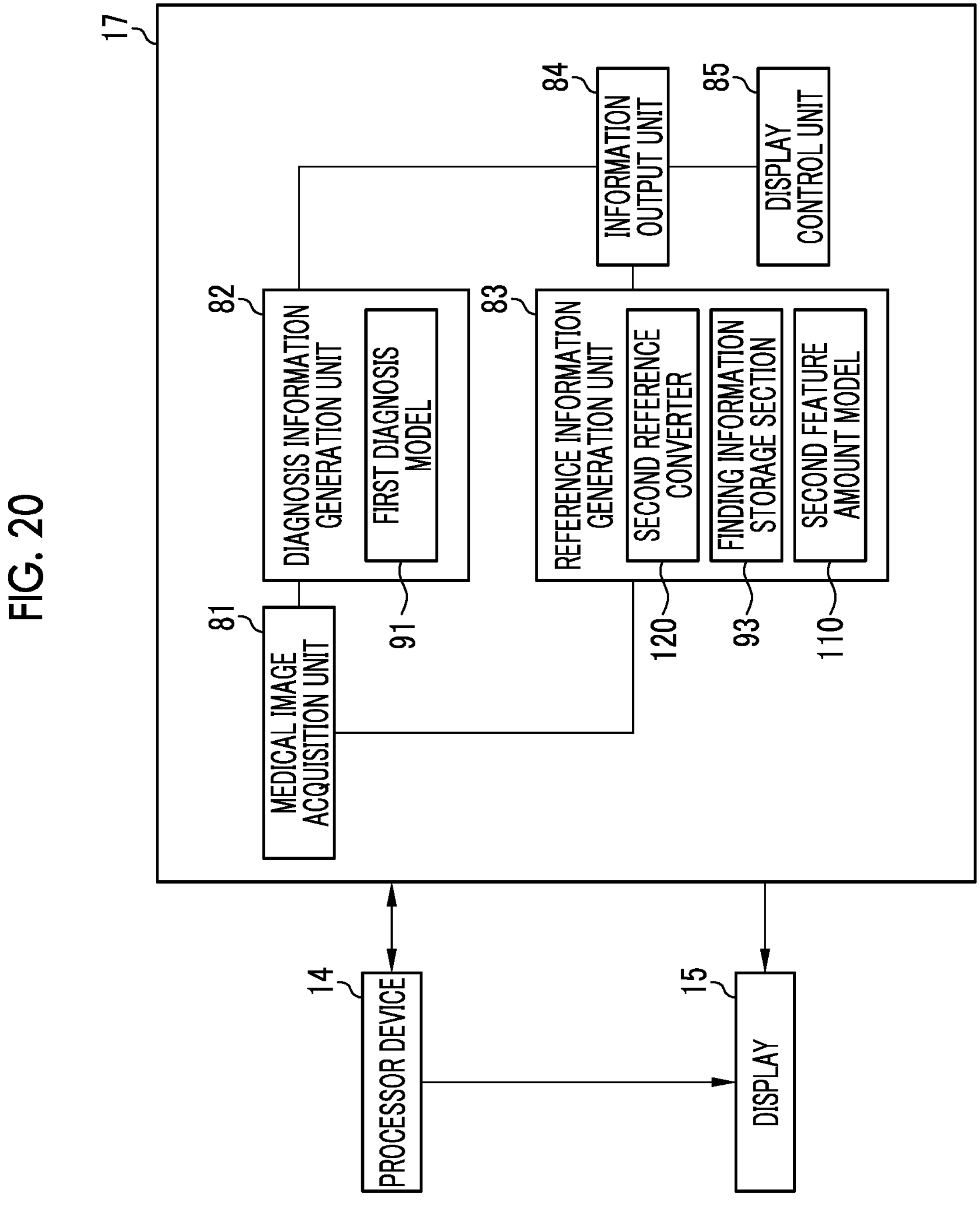
FIG. 20 is a block diagram showing a function of the medical image processing device in which the reference information generation unit comprises a second feature amount model.

As shown in FIG. 20, in this case, the reference information generation unit 83 comprises the second reference converter 120 and a second feature amount model 110. In the diagnosis support observation mode, the medical image acquisition unit 81 sends the first image 72 to the diagnosis information generation unit 82 and sends the normal image 71 captured immediately after the first image 72 to the reference information generation unit 83.

Figure 21:
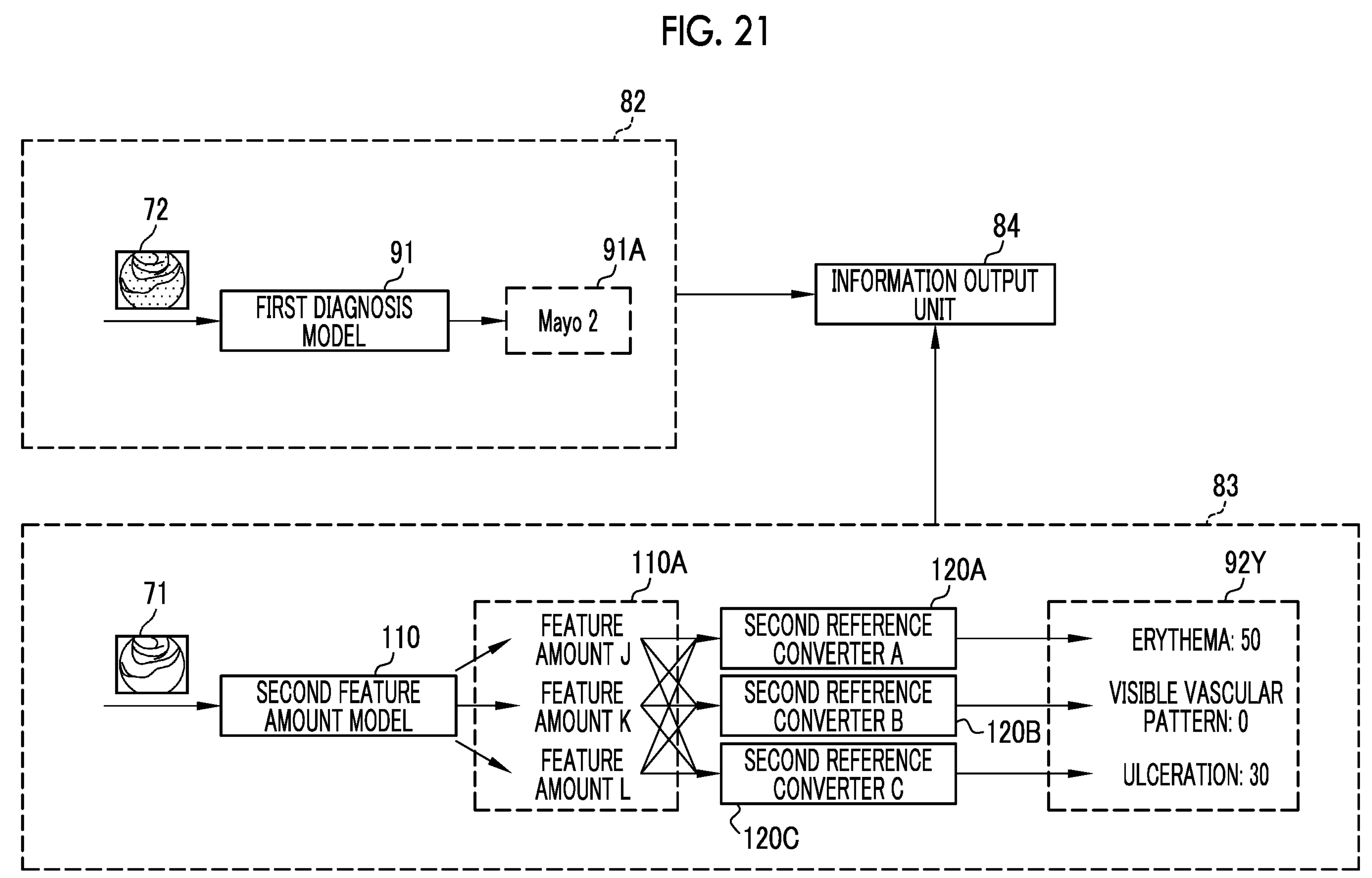
FIG. 21 is an explanatory diagram illustrating a function of the second feature amount model.

As shown in FIG. 21, the diagnosis information generation unit 82 acquires the diagnosis information 91A based on the first image 72 in the diagnosis support observation mode. The details are as described above. Further, it is preferable that the second feature amount model 110 is a learning model in machine learning, which receives an input of the endoscopic image and outputs the feature amount.

As the second feature amount model 110, a model that has been trained and adjusted to output the feature amount in response to an input of the normal image 71 is used. It is preferable that the second feature amount model 110 is a multi-layer neural network model. From the fact that it is a learning model that receives an input of the endoscopic image and outputs the feature amount, the learning model may be a convolutional neural network model or a deep learning model.

Since it is preferable that the second feature amount model 110 receives an input of the normal image 71 showing the same subject as the subject appearing in the normal image 71 having the assigned reference information 94A and outputs the feature amount related to the sub-score such as erythema which is the reference in the Mayo score of ulcerative colitis, the normal image 71 with a pre-assigned sub-score such as erythema, which is the reference of ulcerative colitis, before the diagnosis can be used as training data.

As the feature amount output by the second feature amount model 110, it is preferable that the feature amount having a high correlation with the reference information 92Y can be acquired without limitation. Since the feature amount can be effectively selected in a case where a large amount of feature amounts exist, it is preferable that the second feature amount model 110 acquires the feature amount from the intermediate layer as an autoencoder or acquires the feature amount through clustering. As described above, the second feature amount model 110 can employ various techniques in machine learning in order to acquire the feature amount that has a high correlation with the reference information 92Y and is easy to select in a case of acquiring the feature amount in response to an input of the normal image 71.

One or a plurality of feature amount can be acquired from the second feature amount model 110. In the present embodiment, the second feature amount model outputs three types of feature amounts, that is, a feature amount J, a feature amount K, and a feature amount L. The feature amounts are converted into the reference information 92Y by each of a second reference converter A 120A, a second reference converter B 120B, and a second reference converter C 120C which are prepared.

The second reference converter A 120A, the second reference converter B 120B, and the second reference converter C 120C are generated using the assigned reference information 94A and the feature amount of the normal image 71. The second reference converter 120 is generated by using the feature amount of the normal image 71, unlike the first reference converter 92X, which is generated using the feature amount of the first image 72. In other respects, the second reference converter 120 can be the same as the first reference converter 92X.

In this case, it is preferable that the reference information generation unit 83 acquires the second feature amount of the normal image 71 (second medical image) captured within a preset period before and/or after a time when the first image 72 is acquired, in the diagnosis support observation mode. By setting the above period, it is possible to ensure that the normal image 71 and the second medical image almost reliably show the same subject.

The preset period can be set as follows, for example. In the present embodiment, in a case where the normal light and the first illumination light are automatically switched with 60 fps as a single cycle in the diagnosis support observation mode, for example, the normal image 71, which is the second medical image captured in 40 frames in the first half, and the first image 72, which is the first medical image captured in 20 frames in the second half, are acquired. In the observation in the diagnosis support observation mode, the endoscopic images are captured in a sequence of cycles such as a first cycle (1 second elapsed), a second cycle (2 seconds elapsed), a third cycle (3 seconds elapsed), . . . , an Xth cycle (X seconds elapsed). X is a positive integer.

In a case where the time when the first image 72 is acquired is assumed to be a time when one frame among 20 frames in the second half of the Xth cycle is acquired, a numerical value of n in an X−nth cycle is set as within a preset period before the time when the first image 72 is acquired, and the normal image 71 captured in any one frame among 40 frames in the first half in the X−nth cycle is employed as the second medical image. Similarly, a numerical value of m in an X+mth cycle is set as within a preset period after the time when the first image 72 is acquired, and the normal image 71 captured in any one frame among 40 frames in the first half in the X+mth cycle is employed as the second medical image. n and m are each a positive integer. n or m can be set in advance by a doctor before the examination start.

The selection of which frame of the normal image 71 among 40 frames in the first half to employ can be as follows. For example, among the normal images 71 captured in 40 frames in the first half, a frame with the best image quality, a frame selected randomly, or a frame selected in accordance with a preset rule can be used. As the frame with the best image quality, a frame having no blurriness, water bubbles, halation, or the like can be detected through machine learning, image processing, or the like. Further, as the preset rule, for example, the same frame number can be used for the normal image 71 in accordance with the frame number of the acquired first image 72. Specifically, in a case where the first image 72 is captured in the fifth frame among the first images 72 captured in 20 frames in the second half of the Xth cycle, an image captured in the fifth frame among the normal images 71 captured in 40 frames in the first half of the same Xth cycle as the normal image 71 can be set.

Alternatively, the reference information generation unit 83 may also acquire the second feature amount of the second medical image captured consecutively with the normal image 71. This is because consecutively captured images almost reliably show the same subject.

Figure 22:
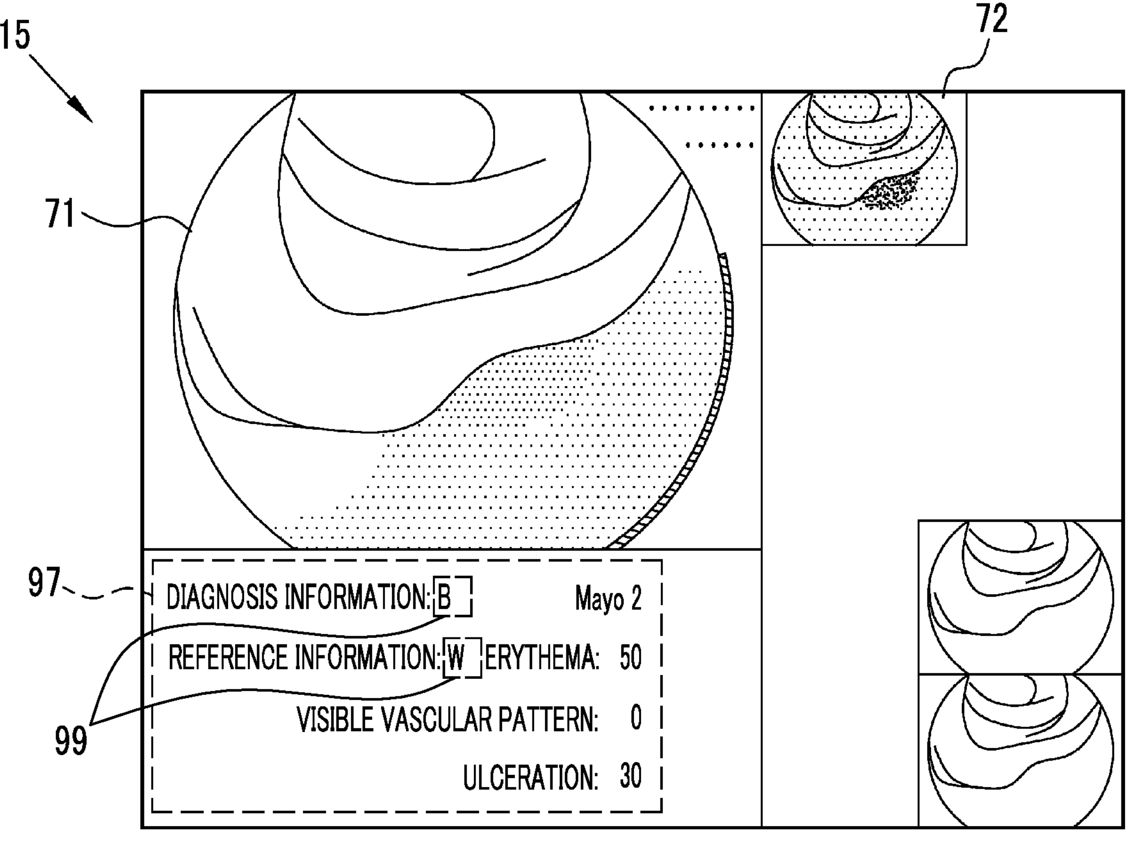
FIG. 22 is an image diagram in which the diagnosis information and the reference information are displayed on the display with the type of an image used added.

In the same manner as described above, the diagnosis information and reference information 97 are sent to the information output unit 84 and displayed on the display 15 by the display control unit 85. As shown in FIG. 22, which type of endoscopic image is input to the CAD to obtain the diagnosis information 91A or the reference information 92Y may be indicated by a rationale image indicator 99. In the present embodiment, since the diagnosis information 91A is acquired through the CAD using the first image 72 and the reference information 92Y is acquired through the CAD using the normal image 71, "B" is displayed on the diagnosis information 91A, and "W" is displayed on the reference information 92Y.

As described above, the endoscopic image obtained through the IEE is used to obtain highly accurate diagnosis information that cannot be obtained only from the normal image 71, for the purpose of obtaining the diagnosis information 91A. Meanwhile, the reference information 92Y associated with the normal image 71, which is normally familiar to the doctor, is obtained for the purpose of obtaining the reference information 92Y. Therefore, both high diagnosis accuracy and high interpretability with respect to the diagnosis result can be obtained.

In the above embodiment, the present invention is applied to a case where processing is performed on the endoscopic image, but the present invention can also be applied to a medical image processing device that processes a medical image other than the endoscopic image, the endoscope system, or the like.

Figure 23:
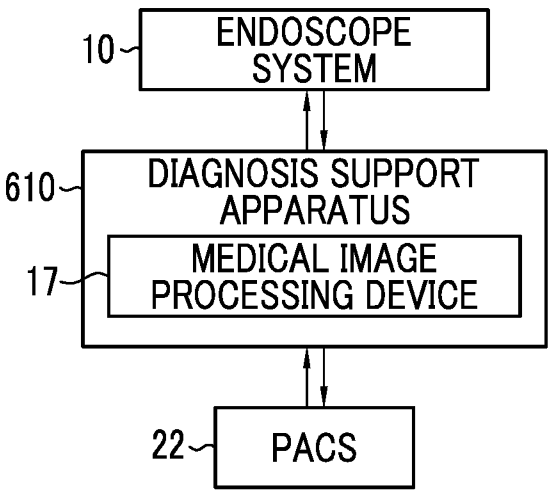
FIG. 23 is an explanatory diagram illustrating a case where the medical image processing device is provided in a diagnosis support apparatus.

Some or all of the image processing unit 55 and/or the central control unit 58 in the endoscope system 10 can be provided in, for example, a diagnosis support apparatus 610 that acquires an image captured by the endoscope 12 directly from the endoscope system 10 or indirectly from a picture archiving and communication systems (PACS) 22. Similarly, as shown in FIG. 23, some or all of the medical image processing device 17 in the endoscope system 10 can be provided in, for example, the diagnosis support apparatus 610 that acquires an image captured by the endoscope 12 directly from the endoscope system 10 or indirectly from the picture archiving and communication systems (PACS) 22.

Figure 24:
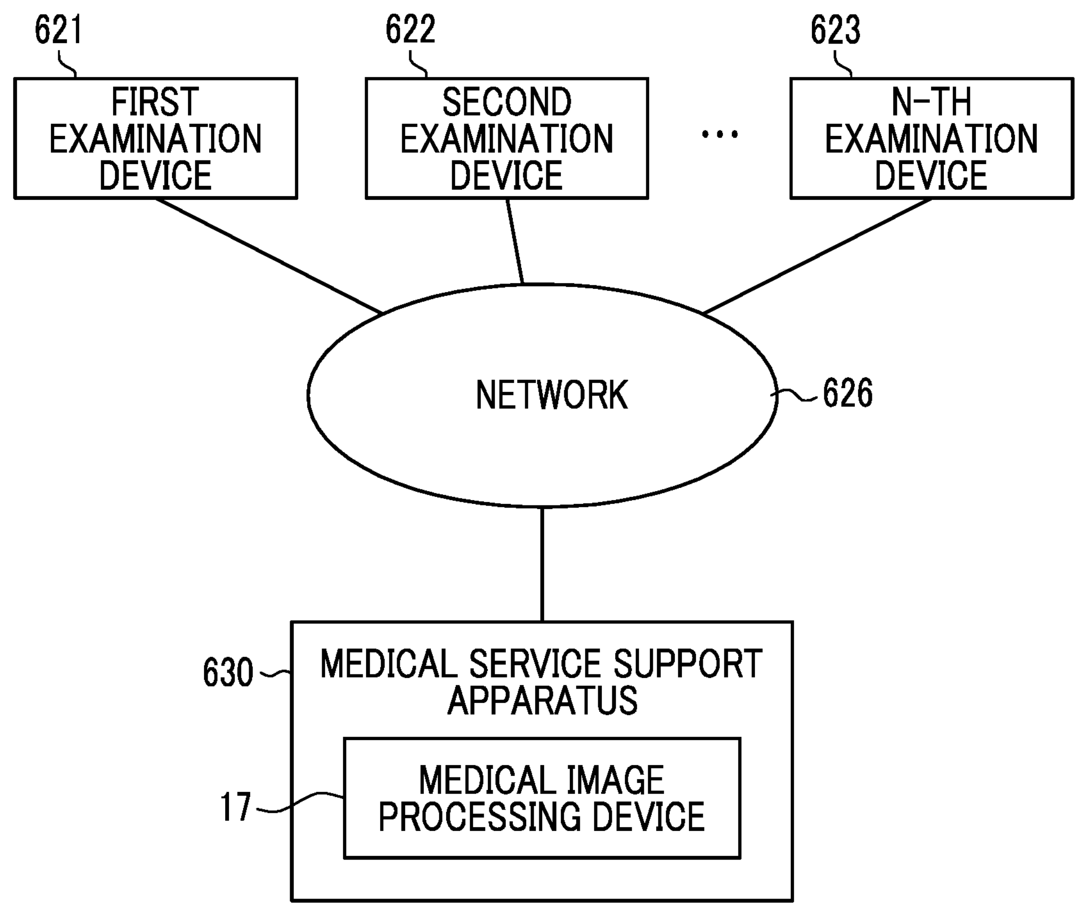
FIG. 24 is an explanatory diagram illustrating a case where the medical image processing device is provided in a medical service support apparatus.

In addition, a medical service support apparatus 630 connected to various examination devices including the endoscope system 10, such as a first examination device 621, a second examination device 622, . . . , and an Nth examination device 623, via a network 626 can be provided with some or all of the image processing unit 55 and/or the central control unit 58, or some or all of the medical image processing device 17 in the endoscope system 10 (for example, see FIG. 24).

In the above embodiment, the hardware structure of the processing unit that executes various types of processing, such as the light source processor, the central control unit 58, the image acquisition unit 51, the DSP 52, the noise reduction unit 53, the memory 54, the image processing unit 55, the display control unit 56, and the video signal generation unit 57, which are provided in the processor device 14 including the first processor, and the medical image acquisition unit 81, the diagnosis information generation unit 82, the reference information generation unit 83, the information output unit 84, and the display control unit 85, which are provided in the medical image processing device 17 including the second processor, is various processors to be shown as follows. The various processors include a central processing unit (CPU) that is a general-purpose processor functioning as various processing units by executing software (programs), a programmable logic device (PLD) that is a processor of which a circuit configuration can be changed after manufacturing, such as a field programmable gate array (FPGA), a dedicated electrical circuit that is a processor having a circuit configuration exclusively designed to execute various types of processing, and the like.

One processing unit may be composed of one of these various processors or may be composed of a combination of two or more processors of the same type or different types (for example, a plurality of FPGAs or a combination of a CPU and an FPGA). Alternatively, a plurality of processing units may be composed of one processor. A first example in which a plurality of processing units are composed of one processor includes an aspect in which one or more CPUs and software are combined to constitute one processor and the processor functions as a plurality of processing units, as represented by a computer such as a client or a server. A second example of the configuration includes an aspect in which a processor that realizes all the functions of a system including a plurality of processing units with one integrated circuit (IC) chip is used, as represented by a system on chip (SoC). As described above, various processing units are composed of one or more of the above various processors, as the hardware structure.

Furthermore, as the hardware structure of the various processors, more specifically, an electrical circuit (circuitry) in which circuit elements, such as semiconductor elements, are combined is used.

EXPLANATION OF REFERENCES

- 10: endoscope system
- 12: endoscope
- 12*a*: insertion part
- 12*b*: operation part
- 12*c*: bending portion
- 12*d*: distal end portion
- 12*e*: angle knob
- 12*f*: zoom operation portion
- 12*g*: mode selector switch

13: light source device
14: processor device
15: display
16: keyboard
17: medical image processing device
20: light source unit
20*a*: V-LED
20*b*: B-LED
20*c*: G-LED
20*d*: R-LED
21: light source processor
22: PACS
30*a*: illumination optical system
30*b*: imaging optical system
41: light guide
42: illumination lens
43: objective lens
44: zoom lens
45: imaging sensor
46: CDS/AGC circuit
47: A/D converter
51: image acquisition unit
52: DSP
53: noise reduction unit
54: memory
55: image processing unit
56, 85: display control unit
57: video signal generation unit
58: central control unit
61: normal image processing section
62: special image processing section
71: normal image
72: first image
81: medical image acquisition unit
82: diagnosis information generation unit
83: reference information generation unit
84: information output unit
91: first diagnosis model
91A: diagnosis information
92: reference converter
92X: first reference converter
92A: first reference converter A
92B: first reference converter B
92C: first reference converter C
92Y: reference information
93: finding information storage section
94: finding information
94A: assigned reference information
95: first feature amount model
95A: first feature amount
96: converter information
97: diagnosis information and reference information
98: lesion region indicator
99: rationale image indicator
100: first feature amount acquisition section
110: second feature amount model
110A: second feature amount
120: second reference converter
120A: second reference converter A
120B: second reference converter B
120C: second reference converter C
610: diagnosis support apparatus
621: first examination device
622: second examination device
623: Nth examination device
626: network
630: medical service support apparatus
ST110 to ST220: step

What is claimed is:

1. A medical image processing device comprising:

one or more processors configured to:

acquire a plurality of types of medical images obtained by imaging a subject under imaging conditions different from each other, wherein a first type of medical image of the plurality of types of medical images is imaged under a first imaging condition of the imaging conditions and a second type of medical image of the plurality of types of medical images is imaged under a second imaging condition of the imaging conditions, as the first imaging condition is imaging under a specific spectrum of light and the second imaging condition is imaging under a normal light which is a broader spectrum than the specific spectrum;

generate, as a first medical image that is the first type of the plurality of types of medical images is input to the one or more processors, diagnosis information regarding a diagnosis of the subject shown in the first medical image;

generate, as a second medical image showing the same subject as the subject shown in the first medical image is input to the one or more processors, reference information regarding a reference for the diagnosis; and output the diagnosis information and the reference information in association with each other, and wherein the reference information is generated using assigned reference information that is the reference information assigned to the second medical image which is the second type of medical image.

2. The medical image processing device according to claim 1, wherein the one or more processors are configured to generate the reference information using the assigned reference information and the medical image showing the same subject as the subject shown in the second medical image to which the assigned reference information is assigned.

3. The medical image processing device according to claim 1, wherein the one or more processors are configured to, in a case where the medical image showing the same subject as the subject shown in the first medical image is input to the one or more processors:

acquire a feature amount of the input medical image; and generate the reference information by converting the feature amount into the reference information.

4. The medical image processing device according to claim 1, wherein the one or more processors are configured to, in a case where the medical image showing the same subject as the subject shown in the first medical image is input to the one or more processors:

acquire a plurality of feature amounts of the input medical image; and generate the reference information by converting the plurality of feature amounts into at least one piece of the reference information.

5. The medical image processing device according to claim 1, wherein the one or more processors are configured to include a first model that generates the diagnosis information, and the first model has a layered structure including a first output layer that outputs the diagnosis information and at least one first intermediate layer.

6. The medical image processing device according to claim 5, wherein the one or more processors are configured to include a second model that generates the feature amount, and the second model has a layered structure including a second output layer that outputs the feature amount and at least one second intermediate layer, and the second intermediate layer shares the first intermediate layer.

7. The medical image processing device according to claim 1, wherein the assigned reference information is the reference information assigned to the second medical image by a doctor through visual observation of the second medical image.

8. The medical image processing device according to claim 1, wherein the one or more processors are configured to, in a case where the first medical image is input to the one or more processors, acquire a first feature amount of the first medical image and generate the diagnosis information based on the first feature amount.

9. The medical image processing device according to claim 8, wherein the one or more processors are configured to generate the reference information by converting the first feature amount into the reference information using the assigned reference information and the first medical image showing the same subject as the subject shown in the second medical image to which the assigned reference information is assigned.

10. The medical image processing device according to claim 1, wherein the one or more processors are configured to, in a case where the second medical image showing the same subject as the subject shown in the first medical image is input to the one or more processors:

acquire a second feature amount of the second medical image; and generate the reference information by converting the second feature amount into the reference information using the assigned reference information and the second medical image.

11. The medical image processing device according to claim 10, wherein the one or more processors are configured to acquire the second feature amount of the second medical image captured within a preset period before and after a time when the first medical image is captured.

12. The medical image processing device according to claim 1, wherein the one or more processors are configured to perform a control of displaying the first medical image and the second medical image on a display.

13. The medical image processing device according to claim 12, wherein the one or more processors are configured to perform a control of displaying the diagnosis information and the reference information, which are associated with each other, on the display.

14. An endoscope system comprising:

a plurality of light sources that emit rays of light having different wavelength ranges;

a processor device that includes a light source processor which is configured to perform a control of emitting each of a plurality of types of illumination light having different combinations of light intensity ratios between the plurality of light sources;

an endoscope that images the subject illuminated with the illumination light; and the medical image processing device according to claim 1.

* * * * *